US006221364B1

(12) United States Patent
Pavelka, Jr. et al.

(10) Patent No.: US 6,221,364 B1
(45) Date of Patent: *Apr. 24, 2001

(54) RECOMBINANT MYCOBACTERIA AUXOTROPHIC FOR DIAMINOPIMELATE

(75) Inventors: Martin S. Pavelka, Jr., Bronx; William R. Jacobs, Jr., City Island, both of NY (US)

(73) Assignee: Albert Einstein College of Medicine of Yeshiva University, Bronx, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/747,177

(22) Filed: Nov. 12, 1996

(51) Int. Cl.[7] .......................... A61K 39/04; C12N 15/64; C12N 1/12; C12N 1/20

(52) U.S. Cl. ...................... 424/248.1; 424/234.1; 424/184.1; 424/200.1; 435/172.1; 435/252.1; 435/253.1; 435/252.3; 435/91.4; 935/65

(58) Field of Search .............................. 424/234.1, 184.1, 424/248.1, 200.1, 172.1; 435/91.4, 252.1, 253.1, 252.3; 935/65

(56) References Cited

U.S. PATENT DOCUMENTS

| | | |
|---|---|---|
| 4,190,495 | 2/1980 | Curtis, III . |
| 5,504,005 | * 4/1996 | Bloom et al. . |
| 5,686,590 | * 11/1997 | Jacobs et al. . |
| 5,773,267 | * 6/1998 | Jacobs et al. . |
| 5,783,386 | * 7/1998 | Jacobs et al. . |
| 5,855,880 | * 1/1999 | Curtiss et al. . |
| 5,972,700 | * 10/1999 | Jacobs et al. . |
| 5,994,137 | * 11/1999 | Jacobs et al. . |

FOREIGN PATENT DOCUMENTS

| | | |
|---|---|---|
| 0080806 | 6/1983 | (EP) . |
| 88 06626 | * 9/1988 | (WO) . |
| 90 00594 | * 1/1990 | (WO) . |
| 90 15873 | * 12/1990 | (WO) . |
| 92 22326 | * 12/1992 | (WO) . |
| WO 95 17511 | * 6/1995 | (WO) . |
| WO 96 25519 | * 8/1996 | (WO) . |

OTHER PUBLICATIONS

Pavelka et al, J. Bacteriol., 178/22:6496–6507, Nov. 1996.*
Wietzerbin et al, Biochemistry, 13/17:3471–76, 1974.*
Bouvier et al, JBC, 259/23:14829–14834, Dec. 1984.*
Cirillo et al, Mol. Microbiol. 11/4:629–639, 1994.*
Kalpana et al, PNAS, 88:5433–5437, Jun., 1991.*
Guleria et al, Nature Medicine, 2/3:334–337, Mar., 1996.*
Pavelka et al, JBC, 269/31:20149–20158, Aug., 1994.*
Cirillo et al, J. Bacteriol, 176/14:4424–29, Jul., 1994.*

Martin S. Pavelka, Jr. et al., entitled "Biosynthesis Of Diaminopimelate, The Precursor Of Lysine And A Component Of Peptidoglycan, Is An Essential Function of Mycobacterium Smegmatis," *Journal Of Bacteriology*, vol. 178, No. 22, pp. 6496–6507 Nov. (1996).

Indira Guleria, et al., entitled "Auxotrophic Vaccines For Tuberculosis," *Nature Medicine*, vol. 2, No. 3, pp. 334–337 Mar. (1996).

William R. Jacobs, Jr., et al., entitled "Introduction Of Foreign DNA Into Mycobacteria Using A Shuttle Phasmid," *Nature*, vol. 327, pp. 532–536 Jun. (1987).

Jeffrey D. Cirillo, et al., entitled "A Novel Transposon Trap For Mycobacteria: Isolation And Characterization Of IS1096," *Journal of Bacteriology*, vol. 173, No. 24, pp. 7772–7780 Dec. (1991).

Jeffrey D. Cirillo, et al., entitled "Isolation And Characterization Of The Aspartokinase And Aspartate Semialdehyde Dehydrogenase Operon From Mycobacteria," *Molecular Microbiology*, vol. 11, No. 4, pp. 629–639 (1994).

Jeffrey D. Cirillo, et al., entitled "Genetic Determination Of The meso–Diaminopimelate Biosynthetic Pathway Of Mycobacteria," *Journal of Bacteriology*, vol. 176, No. 14, pp. 4424–4429 Jul. (1994).

Ganjam V. Kalpana, et al., entitled "Insertional Mutagenesis And Illegitimate Recombination In Mycobacteria," *Proc. Natl. Acad. Sci. USA*, vol. 88, pp. 5433–5437, Jun. (1991).

Frederick C. Neidhardt, et al., entitled "Escherichia Coli And Salmonella Typhimurium," *Cellular And Molecular Biology*, vol. 1 (1987).

J.D. Cirillo, et al., entitled "Molecular Genetic Analysis of Biosynthetic Pathways In Mycobacteria," *Abstracts Of The 90th Annual Meeting Of The American Society For Microbiology*, May 1990 Abstract # U–13 p. 143.

Charles L. Woodley, et al., entitled "Isolalting Specific Auxotrophic Mutants of Mycobacterium Smegmatis By Using Vancomycin", *Antimicrobial Agents And Chemotherapy*, vol. 19, No. 4, Apr. 1981, p. 571–574.

L. Lugosi, et al., entitled "Genetic Transformation Of BCG," *Tubercle* (1989) 70, 159–170.

V.R. Subramanyam, et al., entitled "Partial Characterization of Mycobacterium Fortuitum And Mycobacterium Smegmatis Auxotrophs By Syntrophism Using Bacillus Subtilis", *Journal Of General Microbiology*, vol. 135, Part 10, Oct. 1989, pp. 2651–2654.

V.R. Subramanyam, et al., entitled "Inducibility And Stability Of Auxotrophic Mutations In Mycobacterium Fortuitum, M. Smegmatis And M. Vaccae", *Letters In Applied Microbiology*, 1989, 8, 161–164.

(List continued on next page.)

Primary Examiner—Nita Minnifield
(74) Attorney, Agent, or Firm—Amster, Rothstein & Ebenstein

(57) ABSTRACT

The present invention refers in general to novel recombinant mycobacteria that are auxotrophic for diaminopimelate. In particular, this invention relates to novel auxotrophic recombinant mycobacteria, to methods of making the mycobacteria, and to uses of the mycobacteria to deliver vaccines. This invention also provides for uses of the mycobacteria in drug screening processes.

9 Claims, 7 Drawing Sheets

OTHER PUBLICATIONS

Figure 1:
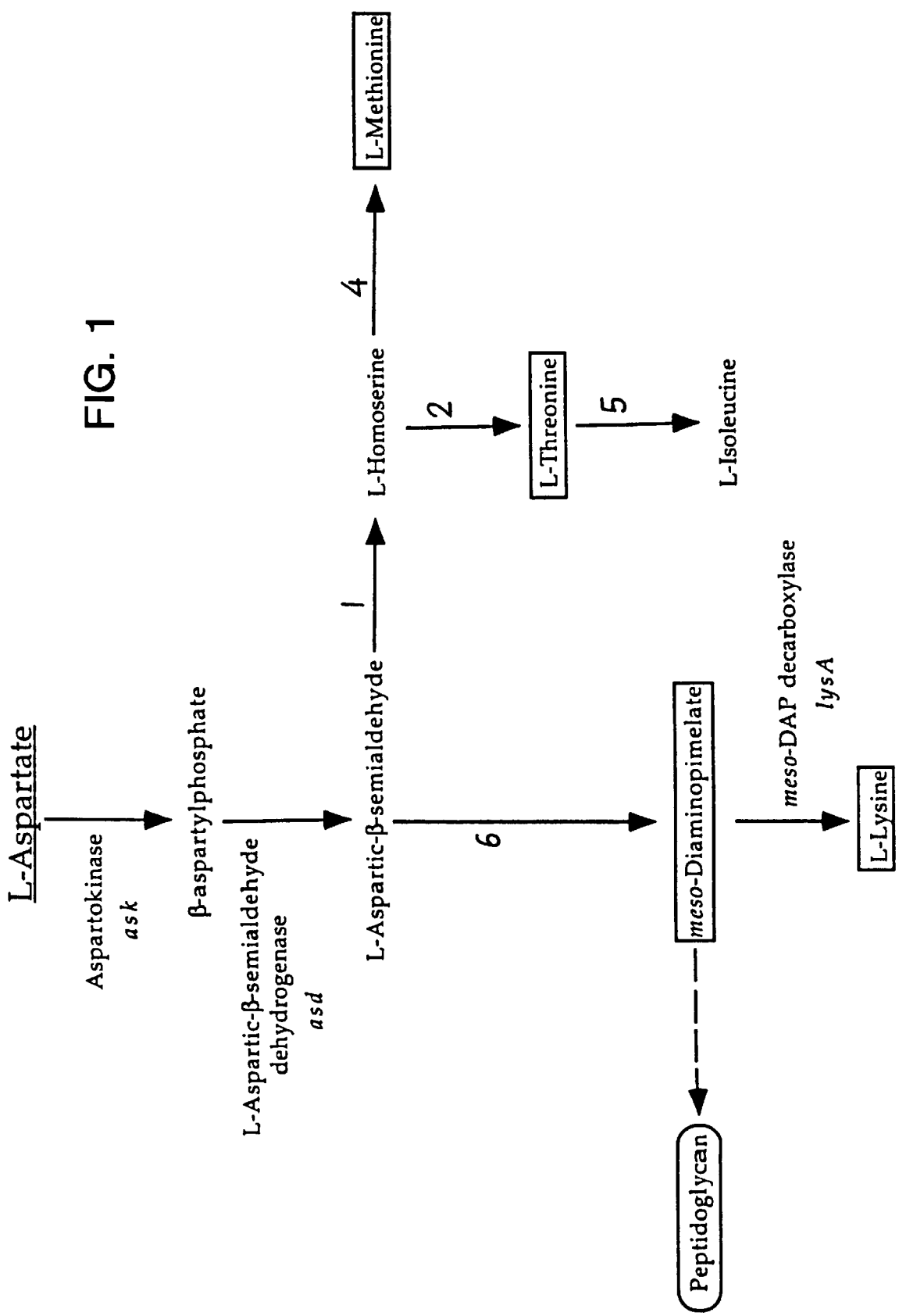

Jeffrey D. Cirillo, et al., entitled "Genetic Determination Of The Meso–Diaminopimelate Biosynthetic Pathway Of Mycobacteria", *Journal Bacteriology*, vol. 179, No. 8, Apr. 1997.

Martin S. Pavelka, Jr., et al., entitled "Cloning Of The DapB Gene, Encoding Dihydrodipicolinate Reductase, From Mycobacterium Tuberculosis", *Journal of Bacteriology*, Apr. 1997, p. 2777–2782, vol. 179, No. 8.

* cited by examiner

SEQUENCE LISTING

```
<160> NUMBER OF SEQ ID NOS:  2

<210> SEQ ID NO 1
<211> LENGTH: 36
<212> TYPE: DNA
<213> ORGANISM: artificial sequence
<220> FEATURE:
<221> NAME/KEY: primer
<222> LOCATION: (1)..(36)
<223> OTHER INFORMATION: used as PCR primer to amplify wild type rpsL
      gene of M. smegmatis

<400> SEQUENCE: 1
atcgttacga ggatccacaa gagaagcaac acacag                                 36

<210> SEQ ID NO 2
<211> LENGTH: 36
<212> TYPE: DNA
<213> ORGANISM: artificial sequence
<220> FEATURE:
<221> NAME/KEY: primer
<222> LOCATION: (1)..(36)
<223> OTHER INFORMATION: used as PCR primer to amplify wild type rpsL
      gene of M. smegmatis

<400> SEQUENCE: 2
tcgattaggc ggatccagca ggaccttgtt cacgag                                 36
```

RECOMBINANT MYCOBACTERIA AUXOTROPHIC FOR DIAMINOPIMELATE

STATEMENT OF GOVERNMENT INTEREST

This invention was made with government support under NIH grants AI26170 and AI33696. As such, the government has certain rights in this invention.

BACKGROUND OF THE INVENTION

Certain mycobacteria represent major pathogens of man and animals. For example, tuberculosis is generally caused in humans by *Mycobacterium tuberculosis,* and in cattle by *Mycobacterium bovis,* which may also be transmitted to humans and other animals. *Mycobacteria leprae* is the causative agent of leprosy. *M. tuberculosis* and mycobacteria of the avium-intracellulare-scrofulaceum group (MAIS group) represent major opportunistic pathogens of patients with acquired immune deficiency syndrome. *M. pseudotuberculosis* is a major pathogen of cattle.

Globally, tuberculosis is the leading cause of death in adults due to an infectious organism (Dolin, et al., *Bull. World Health Organ.* 72: 213–220 (1994)). It is estimated that 90 million new tuberculosis cases resulting in 30 million deaths can be expected during the last decade of this century (Raviglione, et al., *JAMA.* 273: 220–226 (1995)). The resurgence of tuberculosis in developing nations (Snider, et al., *In Tuberculosis: pathogenesis, protection and control.,* B. R. Bloom, (ed.), ASM Press, Washington, D.C. p. 3–11 (1994)), the appearance of multi-drug resistant strains of *Mycobacterium tuberculosis,* and the problem of tuberculosis in the immunocompromised (Haas, D. W. and R. M. Des Prez, *Amer. J. Med.* 96: 439–450 (1994)) call for further study of the mycobacteria. More knowledge about the basic biology of the mycobacteria is needed in order to develop a deeper understanding of the pathogenesis of mycobacterial diseases. Furthermore, identification of biological processes specifically essential for the growth and development of mycobacteria will allow the rational design of drugs to inhibit those processes. The complex cell envelope of the mycobacteria is an outstanding feature of these organisms (Brennan, P. J. and H. Nikaido. *Annu. Rev. Biochem.* 64: 29–63 (1995)). The envelope is composed of a variety of complex lipids including the long chain mycolic acids, and unique polysaccharides such as arabinogalactan and arabinomannan (Besra, G. S. and D. Chatterjee, *Tuberculosis: pathogenesis, protection, and control.,* B. R. Bloom, (ed.), ASM Press, Washington, D.C. p. 285–306 (1994)). These components contribute to the hydrophobic nature of the mycobacterial cell surface (McNeil, M. R. and P. J. Brennan. *Res. Microbiology.* 142: 451–463 (1994)), the low permeability of the mycobacterial cell envelope (Nikaido, H. and V. Jarlier. *Res. Microbiology.* 142: 437–442 (1994), and play a role in the immunological responses of the host to mycobacterial infections (Chan, J. and S. H. E. Kaufmann. *Tuberculosis: pathogenesis, protection, and control.,* B. R. Bloom, (ed.), ASM Press, Washington, D.C. p. 389–415 (1994)).

A specific and important area of interest is the biosynthesis of the peptidoglycan, the innermost layer of the mycobacterial cell wall (Brennan, P. J. and P. Draper. *Tuberculosis: pathogenesis, protection, and control.,* B. R. Bloom, (ed.), ASM Press, Washington, D.C. p. 271–284 (1994)). Peptidoglycan is present in virtually all bacteria providing shape and structural integrity. The peptidoglycan of mycobacteria differs in a few respects from that of other bacteria. In most bacteria the glycan backbone of the peptidoglycan is comprised of N-acetylmuramic acid and N-acetylglucosamine (Ghuysen, J. M., *Bact. Rev.* 32: 425–464 (1968)). In the mycobacteria the former is replaced by N-glycolylmuramic acid (Azuma, et al., *Biochim. Biophys. Acta.* 208: 444–451 (1970). The peptide portion of mycobacterial peptidoglycan is of the common Alg chemotype, consisting of L-Ala-D-Gln-meso-diaminopimelate (meso-DAP)-D-Ala (Schleifer, K. H. and O. Kandler, *Bac. Rev.* 36: 407–477 (1972)), but the glutaminyl and diaminopimelyl residues in the peptide are amidated (Lederer, E., *Pure Appl. Chem.* 25: 135–165 (1971)). The peptidoglycan of *M. leprae* differs from that of other mycobacteria in that the amino acid in position 1 of the peptide is glycine instead of L-alanine (Draper, P., O. Kandler, and A. Darbre., *J. Gen. Microbiol.* 133: 1187–1194 (1987)). As a whole, the mycobacterial peptidoglycan exhibits a high degree of interpeptide crosslinking, primarily through DAP::DAP crosslinks in addition to the DAP:Ala crosslinks more commonly seen in other bacteria (Wietzerbin, et al., *Biochemistry.* 13: 3471–3476 (1974)). In relation to other components of the mycobacterial cell envelope it is known that the mycolyl-arabinogalactan is covalently attached to the peptidoglycan via a unique disaccharide phosphodiester linkage, forming the mycolyl-arabinogalactan-peptidoglycan complex (mAGP) (Besra, et al., *Biochemistry.* 34: 4257–4266 (1995), McNeil, et al., *J. Biol. Chem.* 265: 18200–18206 (1990)).

DAP biosynthesis is central in the structure of the mycobacterial peptidoglycan. DAP is neither produced or required by humans, and thus the DAP biosynthetic pathway is an attractive target for the development of anti-bacterial drugs. DAP auxotrophs of virulent *M. tuberculosis* might prove to be attenuated and therefore, potential live-vaccine strains.

DAP is synthesized by bacteria via the aspartate amino acid family pathway (Umbarger, H. E., *Ann. Rev. Biochem.* 47: 533–606 (1978)). This family is comprised of methionine, threonine, isoleucine, and lysine, amino acids whose carbon skeletons are primarily derived from aspartate. L,L-DAP, or its isomer meso-DAP are intermediates from this pathway used for peptidoglycan synthesis in some bacteria, while meso-DAP is the direct precursor to lysine in all bacteria (Umbarger, H. E., *Ann. Rev. Biochem.* 47: 533–606 (1978)). An aspartokinase enzyme, encoded by the ask gene in mycobacteria, catalyzes the first step in the aspartate family pathway (Cirillo, et al., *Molec. Microbiol.* 11: 629–639 (1994)). Earlier attempts at allelic exchange of the wild type chromosomal ask gene with a disrupted ask allele in *M. smegmatis* to obtain mutants auxotrophic for Met, Thr, and DAP were unsuccessful, suggesting that disruption of ask is lethal to this organism even when the products of the aspartate pathway are present in the culture medium (Cirillo, et., *J. Bacteriol.* 173: 7772–7780 (1991)). Since DNA recombination in mycobacteria is poorly understood, and the failure to obtain a gene disruption is not an absolute measure of the essentiality of that gene, a test to determine if ask is needed.

Accordingly, there exists a need to determine the essentiality of particular genes of mycobacteria in the biosynthesis of the peptidoglycan of the mycobacterial cell wall, as well as in the biosynthesis of other proteins. Once the essentiality of particular genes in these pathways is determined, the need becomes evident for the development of auxotrophic strains of mycobacteria containing mutations in these genes. Mutant mycobacterial strains are required for the biochemical analysis of mycobacteria. As *M. tuberculosis* is an airborne pathogenic mycobacterium, a mutant strain of *M. tuberculosis* that is safe to use in experiments in normal laboratory conditions is extremely desirable. Most significantly, mutant mycobacterial strains have potential therapeutic uses in the prevention and treatment of mycobacterial related diseases and conditions, and more specifically, can be used to deliver vaccines. In addition, there is a need for mutant mycobacterial strains to be developed and used in drug screening processes.

SUMMARY OF THE INVENTION

The present invention provides novel recombinant auxotrophic strains of mycobacteria. Specifically, the present invention provides recombinant strains of mycobacteria that are auxotrophic for diaminopimelate (DAP).

The present invention also provides methods of mutating a mycobacterium. These methods include, for example, methods of illegitimate recombination, legitimate recombination, and transposon insertion.

Further, the present invention provides for the use of the recombinant auxotrophic mycobacteria of the present invention in the prevention and treatment of diseases or conditions associated with mycobacteria, such as the use of these mycobacteria to deliver vaccines.

The present invention also provides for the use of these novel mycobacterial strains in screening drugs.

Additional objects of the invention will be apparent from the description which follows.

BRIEF DESCRIPTION OF THE FIGURES

FIG. 1: FIG. 1 sets forth a schematic of the biosynthetic pathway for the aspartate family of amino acids, as described in the prior art. L-aspartate is the precursor for the synthesis of L-methionine, L-threonine, L-isoleucine, meso-diaminopimelate (DAP), and L-lysine. The first reaction in this pathway is the phosphorylation of L-aspartate by an aspartokinase enzyme, followed by the conversion of b-aspartylphosphate to L-aspartic-β-semialdehyde by a dehydrogenase. In *M. smegmatis,* the ask gene, encoding aspartokinase, is believed to be the promoter proximal gene in an operon with the asd gene encoding L-aspartic-b-semialdehyde dehydrogenase (Cirillo, et al., *Molec. Microbiol.* 11: 629–639 (1994)). L-aspartic-b-semialdehyde is the branchpoint intermediate for the synthesis of the different amino acids in this family. A homoserine dehydrogenase activity (not indicated) converts this intermediate to L-homoserine, which is used for L-methionine, L-threonine and L-isoleucine synthesis. L-aspartic-b-semialdehyde is diverted to diaminopimelate synthesis via dihydrodipicolinate synthase (not indicated), and meso-DAP is the direct precursor for L-lysine. The number of steps in each branch of the pathway is shown in bold. The ask, asd, and lysA genes are indicated.

FIG. 2: FIG. 2 sets forth a schematic drawing of the segregation of DUP1 and recombination products. Homologous recombination between the direct-order repeats of DUP1 will release the intervening DNA sequences resulting in streptomycin resistant recombinants. A cross-over event upstream of the askl::aph insertion (scenario 1) will result in a recombinant with a disrupted ask gene, while a cross-over event downstream of the askl::aph insertion (scenario 2) yields a recombinant with a wild type ask gene.

FIG. 3: FIG. 3 shows a Southern blot of recombinants from DUP1 segregation in the ask asd merodiploid test. Top: maps of pYUB609 integrated into the *M. smegmatis* $mc^2$1255 chromosome (DUP1 [(ORFx ask asd ORFy) *pYUB608*(ORFx askl::aph asd ORFy)], and the recombination products resulting from DUP1 segregation. E=EcoRI, S=SacI restriction endonuclease sites. Bottom, panel A: Southern blot of genomic DNAs from various *M. smegmatis* recombinants and parental strains, digested with SacI and probed with a 919-bp NcoI DNA fragment indicated by the hatched box in the map at the top in the figure. Panel B: The same DNA digests were blotted and probed with the 1.2-kb PstI aph cassette from pYUB609. Note that the central 3.6-kb SacI fragment of the integrated pYUB609 is not detected (n.d.) by these probes. The position and identity of the fragments representing each copy of the ask asd region is indicated on the left while the position of the DNA size markers are on the right (DNA markers: 1-kb ladder, GIBCO/BRL). Lane 1: $mc^2$1255 wild type, lane 2: $mc^2$1255 attB::pYUB643 (ask asd), lane 3: $mc^2$126 5 (DUP1), lane 4: $mc^2$1266 (DUP1 attB::pYUB412), lane 5: $mc^2$1374, a $Sm^f$ $Km^r$ derivative of $mc^2$1266, lane 6: $mc^2$1375, a $Sm^r$ $Km^s$ derivative of $mc^2$1266, lane 7: $mc^2$1268 (DUP1 attB::pYUB643 ask asd), lane 8: $mc^2$1376, a $Sm^r$ $Km^r$ derivative of $mc^2$1268, lane 9: $mc^2$1377, a $Sm^r$ $Km^s$ derivative of $mc^2$1268. The SacI digestion of DNA from $mc^2$1377 was incomplete (lane 9).

FIG. 4: FIG. 4 shows a Southern blot of the *M. smegmatis* askl::aph mutant $mc^2$1278. M: I-BstEII kb markers (NEB). Lanes 1, 4: $mc^2$1255 ask, lanes 2, 5: $mc^2$1212 ask, lanes 3, 6: $mc^2$1278 askl::aph.

FIG. 5: FIG. 5 sets forth a schematic drawing and table of the complementation tests of $mc^2$1278. The map at the top of the figure shows the askl::aph asd region of the *M. smegmatis* $mc^2$1278 chromosome. The direction of transcription of ORFx, ask asd, and ORFy is shown along with the ask asd promoter ($P_{ask\ asd}$) The aph cassette inserted into ask is indicated, with the direction of aph transcription opposite to that of the ask asd operon. The putative terminator downstream of asd is also shown. Maps of the various plasmid subclones in pYUB412 are shown with the results of the complementation test. The mutant was electroporated with the plasmids and transformants selected upon LB DAP medium containing Km and Hyg. The transformants were then patched onto LB Km Hyg medium with or without DAP and scored for the ability to grow in the absence of DAP. Key: +++; very good growth, ++; good growth, –; no growth. Restriction endonuclease sites: E=EcoRI, Ag=AgeI, Ap=ApaLI.

FIG. 6: FIG. 6 shows the "DAP-less death" of $mc^2$1278. The ask mutant was grown to mid-exponential phase in LBT supplemented with 100 mg/ml DAP. The cells were washed and resuspended in fresh LBT with DAP (hatched squares) or without (open squares). The optical density of both cultures was followed for eight hours. After overnight incubation, cells from the saturated culture containing DAP were washed and inoculated into LBT with DAP (hatched circles) or without (open circles). The optical density of these cultures was monitored for ten hours.

FIG. 7: FIG. 7 sets forth a map of the plasmid pYUB328. oriE=ColE1 origin of replication. bla=ampicillin resistance. cosA and cosB=1 cos sequences in tandem, T3 bacteriophage promoter between positions 7 and 37 and T7 bacteriophage promoter between positions 63 and 95. The right side panel is an ethidium bromide stained gel of DNA from the cosmid libraries in pYUB328. Lane 1=λHinDIII marker. Lane 2: BCG library in pYUB328 digested with PstI. Lane 3=BCG library in pYUB328 digested with PacI. Lane 4=*M. tuberculosis* H37Rv library in pYUB328 digested with PstI. Lane 5=*M. tuberculosis* H37Rv library in pYUB328 digested with PacI.

DETAILED DESCRIPTION OF THE INVENTION

The present invention provides for a recombinant strain of mycobacteria that is auxotrophic for diaminopimelate (DAP). As used herein, the term "auxotrophic" recombinant mycobacterium is defined as a mycobacterium having a nutritional mutation whereby the nutritional requirements of the mycobacterium are altered. For example, some auxotrophic mutants are unable to synthesize amino acids, or may require specific amino acids that are not needed by the parental, or prototrophic strain. The term "mutated" as used herein means that the "mutated" mycobacterium possesses at least one mutated gene such that the expression or the function of the gene is varied with respect to the non-mutated gene in the parent strain.

The particular mutation introduced into the mycobacterium typically corresponds to a mycobacterial gene that has been determined by the methods of the present invention to be essential in a biosynthetic pathway of the mycobacterium, and is thus essential for the viability of the mycobacterium. Specifically, the recombinant auxotrophic mycobacteria of the present invention contain mutations in the ask gene, the asd gene, or both the ask and asd genes. These genes have been determined by the methods of the present invention to be essential to the aspartate pathway of mycobacteria. Specifically, the essentiality of these particular genes are determined using the novel counter-selectable marker system of the present invention.

The particular recombinant mycobacterial strains of the instant invention are auxotrophic for diaminopimelate. In particular, the present invention provides for a recombinant auxotrophic mycobacterium that lyses after DAP deprivation. Specifically, the mycobacterial strains of the present invention contain mutations in the aspartokinase (ask) gene, the L-aspartic-β-semialdehyde dehydrogenase (asd) gene, or both the ask and the asd genes to render the mycobacterium auxotrophic for DAP.

The species of recombinant auxotrophic mycobacteria that may be rendered auxotrophic for DAP include, but are not limited to, *M. smegmatis, M. bovis*-BCG, *M. avium, M. phlei, M. leprae, M. fortuitum, M. lufu, M. tuberculosis, M. paratuberculosis, M. habana, M. scrofulaceum,* and *M. intracellulare.*

The methods of the present invention can be used to introduce a mutation into any Mycobacterium species, including, but not limited to, *M. smegmatis, M. bovis*-BCG, *M. avium, M. phlei, M. fortuitum, M. lufu, M. tuberculosis, M. paratuberculosis, M. leprae, M. habana, M. scrofulaceum,* and *M. intracellulare.*

The methods whereby the recombinant mycobacteria of the present invention are mutated include, for example, methods of illegitimate recombination, legitimate recombination, and transposon insertion. The mycobacterium may be mutated through an insertional mutation of a mycobacterial gene. The insertional mutation of the mycobacterial gene may be effected through illegitimate recombination of DNA into the mycobacterial chromosome, or by homologous recombination, or by the insertion of a mycobacterial transposon into a mycobacterial gene, or by the transfection of a mycobacterium with a vector which includes a pair of inverted repeat sequences and DNA encoding a transposase. For specific examples of insertional mutations in mycobacteria, see PCT International Application No. PCT/U.S. Pat. No. 95/06,440, incorporated by reference herein. See also U.S. Pat. No. 5,504,005, incorporated by reference herein. Preferably, the mutation is introduced using long linear recombination substrates, as described in Balasubramian, et al., *J. Bacteriol.* 178:273–279 (1996), incorporated by reference herein.

Where the DNA which is integrated into the mycobacterial chromosome is through illegitimate recombination, the integrated DNA may be a linear DNA fragment or may be a circular DNA. Preferably, the DNA is a linear fragment.

Illegitimate recombination may be effected in mycobacteria by transforming the mycobacteria with a linearized plasmid. Transformation may be accomplished by any means known to those skilled in the art, such as, for example, electroporation, or by the generation of protoplasts into which the transforming DNA is inserted, followed by regeneration of the cell wall, as described in Jacobs, et al. (1987) and Snapper, et al. (1988).

The present invention further provides for vaccine that comprises a recombinant mycobacterium that is auxotrophic for diaminopimelate. The vaccine may contain a mutated ask, a mutated asd gene, or both mutated ask and asd genes. The vaccine of the present invention may be selected from the group of mycobacterial species consisting of *M. smegmatis, M. bovis*-BCG, *M. avium, M. phlei, M. fortuitum, M. lufu, M. tuberculosis, M. paratuberculosis, M. leprae, M. habana, M. scrofulaceum,* and *M. intracellulare.* The recombinant auxotrophic mycobacterial vaccines of the present invention can be used to immunize individuals against diseases such as tuberculosis, leprosy, malaria, diptheria, tetanus, leishmania, salmonella, schistomiasis, measles, mumps, herpes, and influenza. Administration of the recombinant mycobacterial vaccine to a host results in stimulation of the host's immune system to produce a protective immune response.

To form a vaccine, the recombinant auxotrophic mycobacteria of the present invention are administered in conjunction with a suitable pharmaceutical carrier. Representative examples of suitable carriers include, but are not limited to, mineral oil, alum, and synthetic polymers. Vehicles for vaccines are well know in the art and the selection of a suitable vehicle is deemed to be within the scope of those skilled in the art from the teachings contained herein. The selection of a suitable vehicle is also dependent on the manner in which the vaccine is to be administered. The vaccine may be in the form of an injectable dose, and may be administered intramuscularly, intravenously, orally, intradermally, intranasally, or subcutaneous administration. In one embodiment of the invention the vaccine is administered as an aerosol.

Another aspect of the invention involves the use of the recombinant auxotrophic mycobacteria described herein in drug screening processes. Initially, a mutation of a gene of interest is introduced into a mycobacterium, such as *M. smegmatis*. The particular gene of interest is, for example, a gene which has been determined by the methods of the present invention to be essential in a biosynthetic pathway of mycobacteria, and is thus essential for the viability of the mycobacterium. Particular genes of interest are any of the "dap" genes of mycobacteria.

After mutating the gene of interest in *M. smegmatis,* the corresponding gene is removed from *M. tuberculosis* and integrated into the mutated *M. smegmatis* strain. Using this mutated *M. smegmatis* strain for drug screening has several advantages. First, unlike *M. tuberculosis, M. smegmatis* is non-pathogenic and may be used under normal laboratory conditions. Second, *M. smegmatis* grows quickly, whereas *M. tuberculosis* is typically slow growing and therefore is not advantageous for use in drug screening. The initial screen entails growing the mutated mycobacterial strain is grown on agar plates. The compound to be tested is spotted on the lawn of mycobacteria. A clearing of mycobacteria around the spotted test compound demonstrates that the test compound has inhibited the growth of the mycobacteria.

Essentiality of the ask gene in *M. smegmatis*

The essentiality of the biosynthetic pathway for the aspartate family of amino acids in *Mycobacterium smegmatis* was investigated by the experiments described by the present invention. This pathway holds interest because one of its products, diaminopimelate (DAP) is a component of the peptidoglycan, an essential portion of the mycobacterial cell wall. Auxotrophic mutants with lesions in various genes within this pathway have been described for *E. coli* (Thèze, J., et al., *J. Bacteriol.* 117:133–143 (1974)), Salmonella typhimurium (Galán, J. E., et al., *Gene.* 94:29–35 (1990)), *Shigella flexneri* (Sizemore, D. R., et al., *Science.* 270:299–302 (1995)), and *Bacillus megaterium* (Fukuda, A. and C. Gilvarg, *J. Biol. Chem.* 243:3871–3876 (1968)), to name a few. Previous attempts to disrupt ask, the first gene in this pathway, were unsuccessful in *M. smegmatis* (Cirillo, J. D., et al., *J. Bacteriol.* 173:7772–7780 (1991)). In the previous work, a suicide plasmid containing the askl::aph asd fragment and a lacZ reporter gene was used for allelic exchange of ask in the *M. smegmatis* chromosome (Cirillo, J. D., et al., *J. Bacteriol.* 173:7772–7780 (1991)). Integration of this construct into the ask region via a single, homologous recombination event yielded a kanamycin resistant prototrophic clone that was blue when plated on indicator medium. In that experiment, an ask mutant resulting from a secondary recombination event that removed the plasmid sequences (along with the lacZ gene) and left the askl::aph allele in the chromosome could be identified by screening for kanamycin resistant clones that were white on indicator medium. Kanamycin resistant, white clones arose at a frequency of $\sim 10^{-5}$ but were determined to be prototrophs (Cirillo, J. D., et al., *J. Bacteriol.* 173:7772–7780 (1991)). None of the clones had lost the integrated suicide plasmid. Instead, each clone had an novel mobile DNA element (IS1096) inserted into the lacZ gene (Cirillo, J. D., et al., *J. Bacteriol.* 173:7772–7780 (1991)).

The failure to obtain any ask mutants in the earlier work was suggestive, but not proof, that the gene was essential for *M. smegmatis* growing in fully supplemented medium. A similar approach was used for this determination, except that a counter-selectable marker system (streptomycin resistance) was employed instead of a counter-screenable marker system (b-galactosidase activity) and combined with ask merodiploidy in a test of gene essentiality. The strength of the system lies in the ability to select against clones that retain the suicide vector sequences and selecting for those clones that have achieved allelic exchange or retained the wild type allele. The ability to obtain all possible recombinants allows for the analysis of the distribution of phenotypes within the recombinant population. Streptomycin counter selection has been successfully used for allelic exchange in several species of bacteria, including *E. coli* (Russell, C. B. and F. W. Dahlquist, *J. Bacteriol.* 171:2614–2618 (1989)), *Pseudomonas aeruginosa* (Gambello, M. J. and B. H. Iglewski, *J. Bacteriol.* 173: 3000–3009 (1991)), *Yersinia pestis* (Skrzypek, E., et al., *Plasmids.* 29:160–163 (1993)), and more recently, *M. smegmatis* (Sander, P., et al., *Mol. Microbiol.* 16:991–1000 (1995)). The mycobacterial rpsL selection system was developed concurrently with Sander, et al (Sander, P., et al., *Mol. Microbiol.* 16:991–1000 (1995)). The two systems differ in that herein the rpsL gene of *M. smegmatis* driven by a heterologous promoter was used, while the other workers used the rpsL gene of *M. bovis* BCG under control its own promoter (Sander, P., et al., *Mol. Microbiol.* 16:991–1000 (1995)).

More specifically, the counter-selectable marker system of the present invention is based upon the well-known phenomenon that streptomycin resistance mediated by mutations in the rpsL gene, (encoding the S12 ribosomal protein subunit) is recessive to the wild type rpsL gene (Lederberg, J., *J. Bacteriol.* 61:549–550 (1951)). Counter-selection schemes for allelic exchange utilizing rpsL have been successfully demonstrated for a variety of bacteria, including the mycobacteria (Gambello, M. J. and B. H. Iglewski, *J. Bacteriol.* 173:3000–3009 (1991), Russell, C. B. and F. W. Dahlquist, *J. Bacteriol.* 171:2614–2618 (1989), Skrzypek, E., et al., *Plasmids.* 29:160–163 (1993), Sander, P., et al., *Mol. Microbiol.* 16:991–1000 (1995)). The counter-selection system for allelic exchange described here used a strain with a chromosomal mutation in rspL conferring streptomycin resistance (mc$^2$1255), and the wild type rpsL gene cloned in a suicide vector unable to replicate in mycobacteria (pYUB608). To construct the plasmid for allelic exchange of ask, a 6.2-kb DNA fragment containing the ask gene disrupted with a kanamycin resistance marker (askl::aph) was cloned into the rpsL suicide vector pYUB608, yielding pYUB609. The 6.2-kb DNA fragment was derived from pYUB205, the same plasmid used in previous attempts to disrupt ask (Cirillo, J. D., et al., *J. Bacteriol.* 173:7772–7780 (1991)). In the earlier work, pYUB205 was believed to harbor a deletion of asd with the aph cassette replacing the deleted region (Cirillo, J. D., et al., *J. Bacteriol.* 173:7772–7780 (1991)). However, examination of pYUB205 in this study revealed instead that the aph cassette was inserted into a PstI site within ask, in the opposite orientation with respect to the direction of ask asd transcription.

In initial experiments using pYUB609 and mc$^2$1255 (Table 2) Km$^r$ Sm$^r$ askl:aph auxotrophs could not be isolated, either by isolation of Km$^r$ recombinants followed by screening for Km$^r$ Sm$^r$ clones or by direct selection for Km$^r$ Sm$^r$ recombinants. An ask asd merodiploid strain was then used to test if the inability to disrupt ask was due to its essentiality or to the inability to achieve the proper DNA recombinations within the ask region of the chromosome. An ask asd merodiploid was chosen to construct, instead of a strain merodiploid for only ask, since ask and asd are in an operon (Cirillo, J. D. et al., *Molec. Microbiol.* 11:629–639 (1994)) and the aph insertion in the mutant ask allele of pYUB609 would likely have a polar effect upon asd expression. A strain defective for both the ask and asd genes would be phenotypically indistinguishable from a strain with a mutation in either gene alone. Supplying an extra copy of the wild type ask and asd genes elsewhere in the chromosome should allow for the exchange of wild type ask at the normal chromosomal locus with the askl::aph allele. The resultant askl::aph recombinants would not be auxotrophs but disruption of the gene could be confirmed by Southern analysis. For this experiment, a single cross-over recombinant clone was characterized from earlier attempts to disrupt ask in mc$^2$1255 using pYUB609 and streptomycin counter-selection. This strain, mc$^2$1265, is Sm$^s$ Km$^r$ and has pYUB609 integrated in the ask asd region of the chromosome with the rearrangement (DUP1) shown in FIG. 2. The insertion and orientation of pYUB609 in mc$^2$1265 was confirmed by Southern analysis (see FIG. 3, lane 3). An ask asd merodiploid strain was constructed using pYUB412, a vector capable of site-specific integration into the *M. smegmatis* chromosome (Lee, M. H., et al., *Proc. Natl. Acad. Sci.* 88:3111–3115 (1991) and Bardarov, S. and W. R. Jacobs Jr., Unpublished (1995)). A 5-kb DNA insert containing ask asd (see Table 1, below) was cloned into pYUB412, producing pYUB643. Strain mc²1268 was constructed by site-specific integration of the ask asd carrying plasmid pYUB643 (hyg) into the chromosome of strain mc²1265 (rpsL4 DUP1, Sm$^s$ Km$^r$). Strain mc²1266 is an isogenic control made by integration of the vector pYUB412 (hyg) into the chromosome of strain mc²1265. The different ask asd regions are of different sizes and easily distinguished from each other in Southern analysis. The strains mc²1268 and mc²1266 were used in the allelic exchange experiment.

TABLE 1

Plasmids used in this study

| Plasmid | Description |
|---|---|
| pKSII⁺ | Ap$^r$, high-copy number cloning vector, ColE1, unable to replicate in mycobacteria (Stratagene) |
| pMV261 | Km$^r$, *E. coli*-mycobacteria shuttle vector, contains the hsp60 promoter, ColE1, OriM |
| pET3d.lysA | *M. tuberculosis* Erdman lysA gene cloned into pET3d |
| pYUB114 | 5-kb EcoRI fragment from *M. smegmatis* mc²6 containing ORFx ask asd ORFy cloned into the EcoRI site of pKSII⁺ |
| pYUB205 | pYUB114 with a 1.2-kb aph cassette inserted into a PstI site within the ask gene, Km$^r$ |
| pYUB412 | Ap$^r$, Hyg$^r$, *E. coli*-mycobacteria shuttle vector, ColE1 origin, int attP non-replicative but integration-proficient in mycobacteria |
| pYUB558 | pKSII⁺ containing the major P$_{left}$ promoter of mycobacteriophage L5 |
| pYUB600 | pMV261 containing the *M. smegmatis* mc²155 rpsL gene PCR product under control of the hsp60 promoter. |
| pYUB608 | 465-bp MscI-ClaI rpsL fragment from pYUB600 cloned into the HincII-ClaI sites of pYUB558, rpsL under control of the major P$_{left}$ promoter of mycobacteriophage L5 |
| pYUB609 | 6.3-kb EcoRI fragment from pYUB205 containing ORFx ask::aph asd ORFy cloned into the EcoRI site of pYUB608 |
| pYUB628 | 1.3-kb XhoI-BamHI fragment from pET3d.lysA cloned into the PvuII-BclI sites of pMV261, lysA under control of the hsp60 promoter |
| pYUB643 | 5-kb EcoRI fragment from pYUB114 containing ORFx ask asd ORFy cloned into the EcoRV site of pYUB412 |
| pYUB646 | 3.5-kb EcoRI-AgeI fragment from pYUB114 containing ORFx ask asd cloned into the EcoRV site of pYUB412 |
| pYUB647 | 2.8-kb EcoRI-ApaLI fragment from pYUB114 containing ORFx ask cloned into the EcoRV site of pYUB412 |
| pYUB651 | 2.2-kb NotI-SspI fragment from pYUB628 containing P$_{hsp60}$ lysA cloned into the EcoRV site of pYUB412 |

Figure 2:
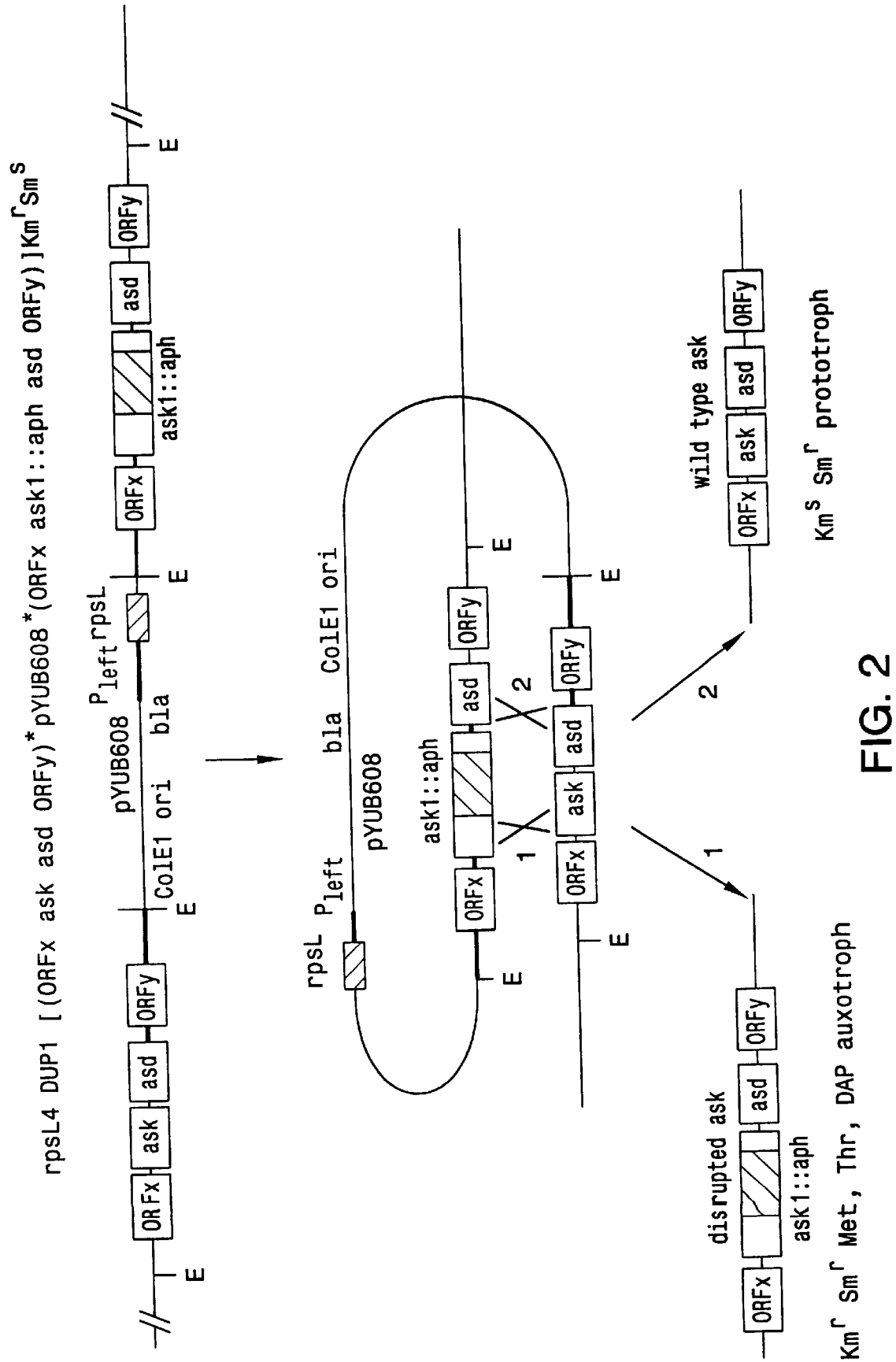

The rationale of the essentiality test is as follows. The control strain mc²1266 has pYUB609 integrated into the ask asd region of the chromosome, resulting in direct-ordered repeats of the ask asd region (DUP1), and a Sm$^s$ Km$^r$ phenotype (FIG. 2). At a particular frequency, the repeats in DUP1 will undergo homologous recombination with each other and the ask alleles will segregate (FIG. 2). Recombinants that retain the askl::aph allele will be Sm$^r$ Km$^r$ mutants auxotrophic for Met, Thr, and DAP; recombinants with the wild type gene will be Sm$^r$ Km$^s$ prototrophs. If ask is essential, only the wild type ask Sm$^r$ Km$^s$ recombinants are expected to be obtained. Strain mc²1268, the Sm$^s$ Km$^r$ ask asd merodiploid strain, has an extra copy of wild type ask and asd located at attB; therefore both recombinant types should be seen. The frequency of the two recombinant classes (Sm$^r$ Km$^r$; Sm$^r$ Km$^s$) should be similar because the amount of homologous DNA flanking the askl::aph allele in pYUB609 is similar (1.9-kb upstream and 3.0-kb downstream).

To determine the recombination frequencies for this test, three separate cultures of each strain were grown to late logarithmic phase in LBT supplemented with hygromycin (Hyg) and DAP. The cultures were diluted and plated for the number of viable colony forming units/ml on LB DAP, LB DAP Sm, and LB DAP Sm Km media. The results from these experiments reveal that the averaged frequency of streptomycin resistance was $10^{-3}$ for both strains, while the averaged frequency of Sm$^r$ Km$^r$ was $10^{-4}$ (see Table 4, compare strain mc²1266 to strain mc²1268). The phenotypes of one hundred streptomycin resistant clones from each culture was tested for kanamycin resistance and relevant auxotrophy, and also verified that each recombinant remained Sm$^r$ (due to segregation of DUP1) and Hyg$^r$ (due to the plasmid integrated at attB). As shown in Table 3, the strain lacking an additional copy of ask and asd at the attB locus (mc²1266) formed few Sm$^r$ Km$^r$ recombinants (3%±1%) and none of these Sm$^r$ Km$^r$ recombinants had the expected auxotrophy of an ask mutant. The strain containing an addition copy of ask and asd at attB (mc²1268) frequently yielded Sm$^r$ Km$^r$ recombinants (50%±4%), indicating that recombination at the ask locus readily occurs. As expected if ask is essential, mc²1268 yielded an equivalent distribution between Sm$^r$ Km$^r$ and Sm$^r$ Km$^s$ recombinants while virtually all the clones from the control strain mc²1266 were Sm$^r$ Km$^s$. None of the directly selected Sm$^r$ Km$^r$ recombinants exhibited auxotrophy (Table 3). These findings indicate that segregation of DUP1 can only yield an ask insertion mutant if an extra copy of ask asd are present at another chromosomal site.

Figure 3:
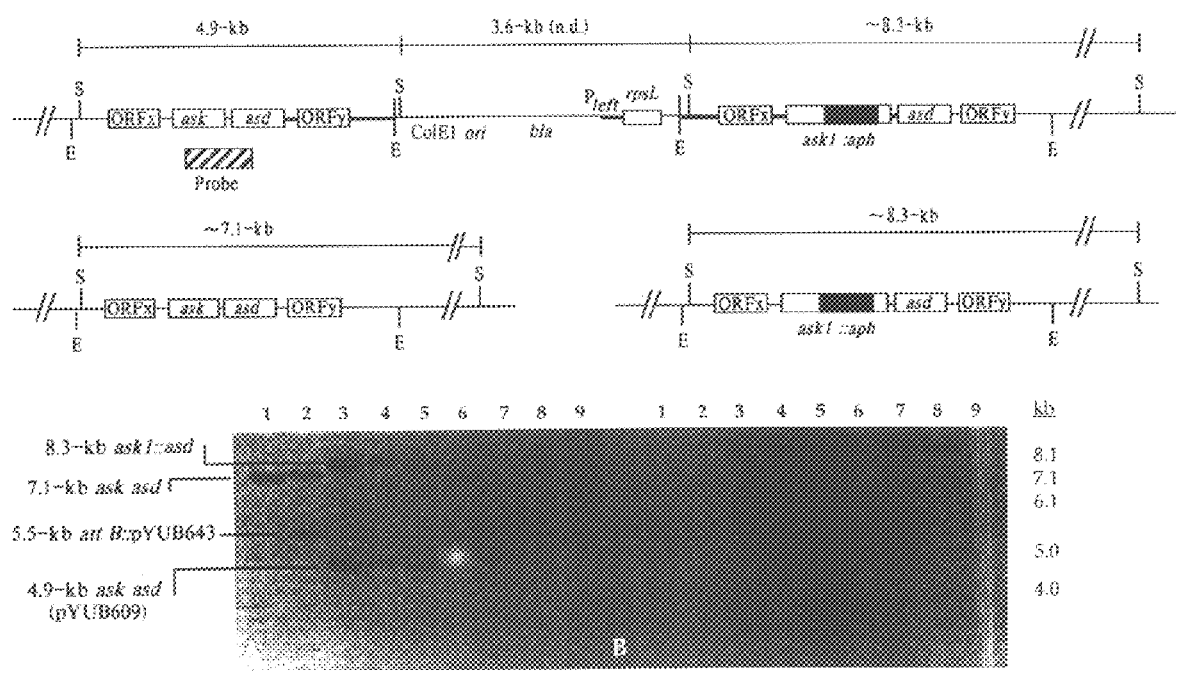

To confirm the genetic organization of the recombinants, Southern analysis was performed on the parental strains and the Sm$^r$ recombinants (FIG. 3). The different ask asd regions in the chromosomes of the parent strains can be easily distinguished (see maps at the top of FIG. 3). The blot in FIG. 3, panel A, is a collection of genomic DNAs digested with SacI and probed with an 'ask asd' containing fragment of DNA. The first 3 lanes contain DNA from the parental strains and a control strain which is necessary for determining the appearance of each ask asd region. The wild type strain mc²1255 (lane 1) shows a single band of ~7.1-kb corresponding to the wild type ask asd region in the chromosome. Lane 2 is mc²1255 with ask asd of pYUB643 integrated at the attB site, showing the additional fragment of 5.5-kb indicative of the attB copy. Lane 3 contains DNA from the strain mc²1265, which has the direct-order duplication DUP1 [(ORFx ask asd ORFy)*pYUB608*(ORFx askl::asd ORFy)]. For this strain, mc²1265, a fragment of 4.9-kb corresponds to the wild type ask asd copy, while the upper band at ~8.3-kb corresponds to the copy with the askl::aph allele. The vector of plasmid pYUB609 has a SacI site nearby the copy of wild type ask asd; reducing the size of the SacI fragment of the wild type ask asd region from ~7.1-kb down to 4.9-kb (see map, FIG. 3, top). Lane 4 has a digest of strain mc²1266 (DUP1 attB::pYUB412) and lane 7 has a digest of mc²1268, (DUP1 attB::pYUB643 ask asd), the ask asd merodiploid strain. The three different ask asd regions are clearly distinguishable from each other in lane 7. Lanes 5 and 6 represent recombinants derived from strain mc²1266 (DUP1 attB::pYUB412). Lane 5 shows that mc²1374, a Sm$^r$ Km$^r$ clone, has the same pattern as its parental strain mc²1266 (see lane 4) and therefore did not segregate DUP1. This recombinant may have been formed by a gene conversion event between the two rpsL genes resulting in two Sm$^r$ alleles. A similar phenomenon of background streptomycin resistance was noted by other workers utilizing this type of counter-selection system in *E. coli* (54). In contrast, Lane 6 shows that mc²1375 a Sm$^r$ Km$^s$ recombinant derived from mc²1266 (DUP1 attB::pYUB412) formed by segregation of DUPl and retention of the wild type ask gene, as expected. A comparison between lane 6 and lane 1 shows that recombinant mc²1375 has only the ~7.1-kb fragment that corresponds to the wild type copy of ask asd. Strain mc²1268 (DUP1 attB-::pYUB643 ask asd) should form two classes of Sm$^r$ recombinants, depending upon the ask allele that is retained after DUP1 segregation. The Sm$^r$ Km$^r$ recombinants retain the askl::aph allele; whereas the Sm$^r$ Km$^s$ recombinants retain the wild type allele. Both of these recombinant classes have pYUB643 (ask asd) at attB. Lane 8 is mc²1376, a Sm$^r$ Km$^r$ derivative of mc²1268 which lacks the wild type ask asd-specific fragment of ~7.1-kb, but has the ~8.3-kb fragment indicative of askl::aph asd, as well as the copy of ask asd at the attB site (the 5.5-kb fragment). Lane 9 shows the pattern for mc²1377, a Sm$^r$ Km$^s$ derivative of mc²1268. This strain has the wild type ask asd-specific fragment (~7.1-kb) and the 5.5-kb ask asd fragment at the attB site. To confirm the location of the askl::aph alleles, the same genomic DNAs were probed with the aph gene (FIG. 3, panel B). As expected, this probe hybridized only to the ~8.3-kb fragment of the Km$^r$ strains (lanes 3,4,5,7, and 8). In addition these DNAs were probed with pKSII$^+$ (the vector of pYUB608). No pKSII$^+$-specific hybridization signals were seen with genomic DNA from mc²1375, mc²1376 and mc²1377, confirming that these recombinants had undergone DUP1 segregation and lost the pYUB609 vector sequences.

Disruption of ask in a lysine auxotroph of *M. smegmatis*

The inventors have shown that the ask gene of *M. smegmatis* cannot be disrupted unless the strain is merodiploid for ask and asd. Based upon the fact that *M. smegmatis* mutants auxotrophic for all other amino acids of the aspartate family exist, the inventors concluded that DAP must be the limiting metabolite preventing survival of an ask mutant. The inventors believe that the essentiality of DAP synthesis results from the fact that DAP has the dual distinction of being both a component of the peptidoglycan as well as the direct precursor to lysine. The inventors propose that the transcription of the lysA gene, encoding meso-DAP decarboxylase, is not sufficiently repressed when the organism is growing in rich medium. In addition, the inventors propose that the intracellular DAP pool derived from exogenous DAP may be less than that which is normally obtained from exogenous synthesis in wild type cells. The effect of basal level DAP-decarboxylase activity upon a large DAP pool present in wild type cells would be small compared to the effect upon a smaller pool present in a DAP auxotroph. Therefore, in the early development of an ask mutant, a significant fraction of the limited amount of DAP taken up into the cell is converted to lysine, resulting in an insufficient amount of DAP to support peptidoglycan synthesis.

There is no barrier to mutation of ask or asd (or their homologs) in organisms such as *E. coli* and *Salmonella typhimurium* (Galán, J. E., et al., *Gene.* 94:29–35 (1990), Thèze, J., et al., *J. Bacteriol.* 117:133–143 (1974)). Mutations within these genes results in strains auxotrophic for Met, Thr, and DAP. Mutants of *M. smegmatis* exist which are auxotrophic for Met, Thr, Ile, and Lys (McKinney, J. D., F. C. Bange, and W. R. Jacobs Jr. 1995. Unpublished), therefore the inventors focused on DAP as the essential metabolite of this pathway. Other workers have reported an inability to obtain DAP auxotrophs of the related bacteria *Corynebacterium glutamicum* (Cremer, J., et al., *J. Gen. Microbiol.* 134:3221–3229 (1988)). The explanation given for this phenomenon was that *C. glutamicum* is incapable of transporting DAP from the medium ((Cremer, J., et al., *J. Gen. Microbiol.* 134:3221–3229 (1988)). An absolute inability to transport DAP would not appear to be the reason for the presumed essentiality of DAP synthesis in *M. smegmatis*, as mc²155 grows well in glucose-salts minimal medium with DAP as the sole nitrogen source. Therefore, another reason was sought to explain why ask disruption and subsequent DAP auxotrophy would be lethal to *M. smegmatis*. Since meso-DAP is used for both lysine synthesis and peptidoglycan synthesis, it was theorized that ask disruption is lethal to *M. smegmatis* because the extracellular meso-DAP taken up from the medium is converted to lysine, due to insufficient repression of lysA, the gene encoding DAP-decarboxylase (FIG. 1). This hypothesis is supported by reports that expression of lysA is constitutive in the corynebacteria, close relatives of the mycobacteria (Marcel, T., et al., *Mol. Micobiol.* 4:1819–1830 (1990), Oguiza, J. A., et al., *J. Bacteriol.* 175:7356–7362 (1993)). Wild type mycobacterial cells may have a large intracellular DAP pool derived from endogenous synthesis, and the fraction converted to lysine by a low, but constitutive DAP-decarboxylase activity too small to affect peptidoglycan synthesis and cell integrity. However, a mutant with a newly disrupted ask gene, now dependent upon exogenous DAP, may not be able to transport enough DAP to achieve a intracellular DAP pool as large as that in wild type cells, thus the basal level DAP-decarboxylase activity may divert a significant fraction of the pool away from peptidoglycan synthesis leading to death of the cell.

It is anticipated that a *M. smegmatis* Lys$^-$ auxotroph unable to convert meso-DAP to lysine would accumulate a large intracellular pool of meso-DAP reserved for peptidoglycan synthesis and be permissive for ask disruption. To test this hypothesis, the ability to disrupt ask in strain mc²1212 (lysA rpsL5) and strain mc²1270 (lysA$^+$ rpsL5) was compared. The latter strain is an isogenic, spontaneous Lys$^+$ derivative of mc²1212. Allelic exchange of ask in these strains was attempted by two methods; either by direct selection of Km$^r$ recombinants followed by identification of Km$^r$ Sm$^r$ auxotrophs, or by direct selection of Km$^r$ Sm$^r$ recombinants and screening for auxotrophy. The two strains were electroporated with pYUB609 in duplicate with one transformation mixture plated onto LB DAP Km medium, and the other plated onto LB DAP Km Sm medium. As shown in Table 2, both strains yielded kanamycin resistant recombinants at a similar frequency after direct selection on kanamycin medium. The number of those Km$^r$ clones that were also Sm$^r$ was higher for the Lys$^+$ strain mc²1270 than for the Lys$^-$ strain mc²1212. However, only the Lys$^-$ strain mc²1212 yielded mutants auxotrophic for Met, Thr and DAP (see Table 2). Likewise, direct selection for Km$^r$ Sm$^r$ yielded similar frequencies for recombinants from both strains, but ask disruption was only seen in the Lys$^-$ strain (Table 2).

To confirm these results, the ability to achieve ask disruption in isogenic Lys$^+$ and Lys$^-$ strains which had integrated pYUB609 (ORFx askl::aph asd ORFx) into the ask region of the chromosome was compared. For these experiments, a Km$^r$ Sm$^s$ pYUB609 plasmid-chromosome recombinant of mc²1212 (Lys$^-$) and mc²1270 (Lys$^+$) from the experiment shown in Table 2 was isolated and examined. Each recombinant has pYUB609 integrated in the same fashion previously described for the ask asd chromosomal rearrangement DUPl [(ORFx ask asd ORFy)*pYUB608* (ORFX askl::aph asd ORFy)], (see FIG. 2). The Lys$^-$ strain with integrated pYUB609 is mc²1269 (lysA rpsL5 DUP1), while the Lys$^+$ strain with an integrated pYUB609 is mc²1276 (lysA$^+$ rpsL5 DUP1). It was determined if the askl::aph insertion could be retained in both strains following segregation of DUP1. Duplicate cultures of strain mc²1269 (lysA rpsL5 DUP1) and strain mc²1276 (lysA⁺ rpsL5 DUP1) were grown in LBT supplemented with DAP and plated out for viable cfu/ml and colonies were tested for antibiotic resistance and auxotrophic phenotype (Table 3). As expected, the Lys⁻ strain mc²1269 yielded Sm$^r$ Km$^r$ auxotrophic ask mutants by either direct selection for Sm$^r$ recombinants or Sm$^r$ Km$^r$ recombinants (Table 3). The Lys⁺ strain formed Sm$^r$ recombinants at a frequency comparable to the isogenic Lys⁻ mutant, but the frequency of Sm$^r$ Km$^r$ recombinants was slightly less. None of the Lys⁺ recombinants tested had an auxotrophic phenotype (Table 3).

To further examine the Lys⁺ phenotype as a barrier to ask disruption, a derivative of mc²1212 was constructed that is Lys⁺ due to the presence of a wild type copy of lysA. The plasmid pYUB651 was constructed from the integrating vector pYUB412 and harbors the lysA gene of *M. tuberculosis* under control of the hsp60 promoter. This plasmid was electroporated into the strain mc²1269 (lysA rpsL5 DUP1) resulting in the strain mc²1386, which is phenotypically Lys⁺. The strain mc²1269 (lysA rpsL5 DUP1) containing pYUB412 served as the Lys⁻ control strain mc²1385. The recombinants obtained from these two strains after DUP1 segregation were examined in duplicate experiments done in a similar manner as previous experiments (see Table 3). Km$^r$ Sm$^r$ ask auxotrophs were obtained only from the Lys⁻ control strain mc²1385 (lysA rpsL5 DUP1 attB::pYUB412). No auxotrophs were obtained from experiments using the phenotypically Lys⁺ strain mc²1386 (lysA rpsL5 DUP1 attB::pYUB651). The Sm$^r$ Km$^r$ derivatives from both strains were patched onto defined medium (Middlebrook 7H9) containing hygromycin and the appropriate supplements with or without lysine to confirm the Lys phenotype of each clone. All clones were hygromycin resistant and had maintained the Lys phenotype of their respective parental strain.

To determine if ask could be physically disrupted in the strain mc²1270, the isogenic Lys⁺ revertant of mc²1212, the products from DUP1 segregation in the strain mc²1276 (lysA⁺ rpsL5 DUP1), with or without an extra copy of ask asd were analyzed. The experiment was essentially the same as for the mc²1255 merodiploid test. Duplicate cultures of strain mc²1387 (lysA⁺ rpsL5 DUP1 attB::pYUB412) and strain mc²1388 (lysA⁺ rpsL5 DUP1 attB::pYUB643 ask asd) were grown to late logarithmic phase in LBT DAP supplemented with Hyg, plated onto various selective media and screened for antibiotic resistance and auxotrophy. The results are shown in Table 3. From mc²1387 (lysA⁺ rpsL5 DUP1 attB::pYUB412), only 3% Sm$^r$ Km$^r$ clones (none of which were auxotrophs) were obtained from the directly selected Sm$^r$ clones. None of the directly selected Sm$^r$ Km$^r$ recombinants were auxotrophic. However, from the strain mc²1388 (lysA⁺ rpsL5 DUP1 attB::pYUB643 ask asd), directly selected Sm$^r$ recombinants yielded Sm$^r$ Km$^r$ clones at a frequency of 63%±20% (Table 3). As in the case for the wild type strain mc²1255, the Lys⁺ revertant of mc²1212 appears permissive for ask disruption only when provided with an extra copy of ask and asd.

Characterization of the ask mutant mc²1278, a DAP auxotroph

Figure 4:
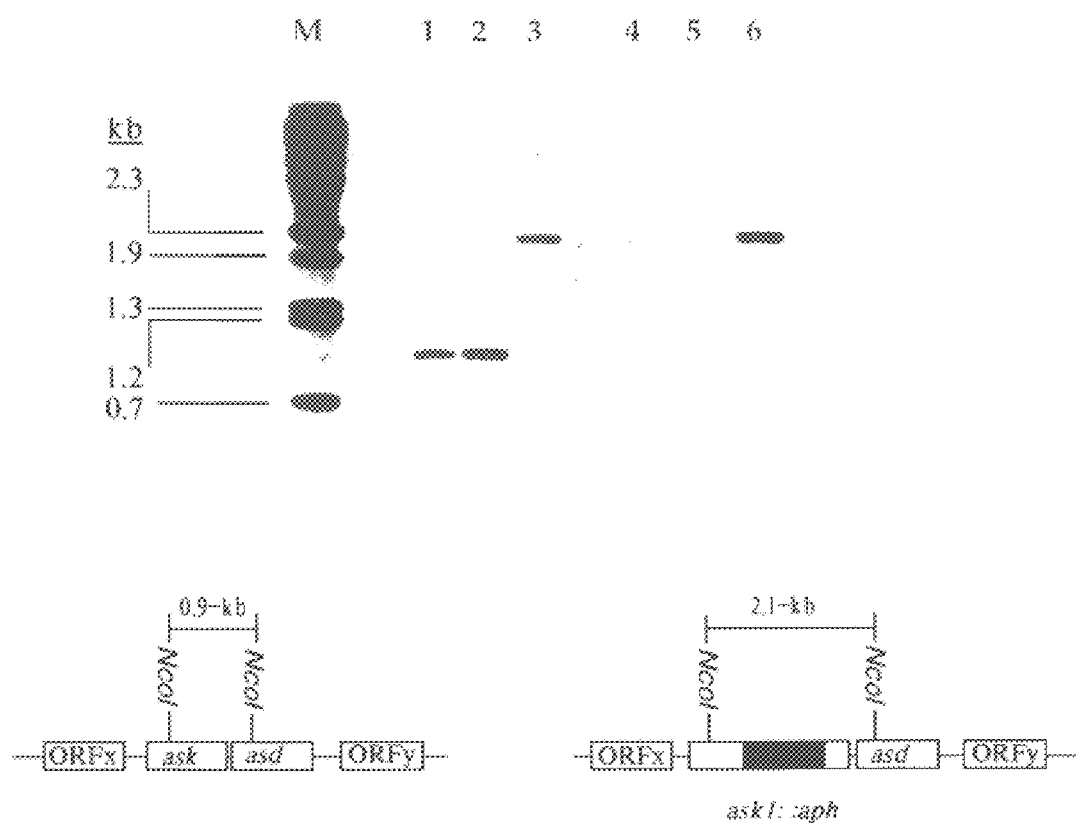

One of the askl::aph mutants obtained by direct selection for Km$^r$ Sm$^r$ recombinants following electroporation of pYUB609 into mc²1212 (Table 2) was chosen for further study and designated mc²1278. This strain is auxotrophic for Met, Thr, DAP, and Lys as expected for an ask mutation in this particular background. To confirm the allelic exchange of ask, mc²1278 was analyzed by Southern hybridization. FIG. 4, lanes 1,2 and 3 show genomic DNA prepared from mc²1255, mc²1212 and the ask mutant mc²1278, digested with NcoI and probed with a 0.9-kb NcoI fragment spanning ask and asd. The fragment containing the wild type gene is 0.9-kb in size, while the fragment bearing the askl::aph allele is 2.1-kb. mc²1278 clearly shows the expected shift in size (+1.2-kb) for the disrupted askl::aph allele (FIG. 4, lane 3). To confirm the identity of this fragment, the same NcoI-digested DNA samples were probed with the aph cassette (FIG. 4, lanes 4, 5, and 6). This probe hybridized only to the 2.1-kb fragment of mc²1278 (FIG. 4, lane 6).

Figure 5:
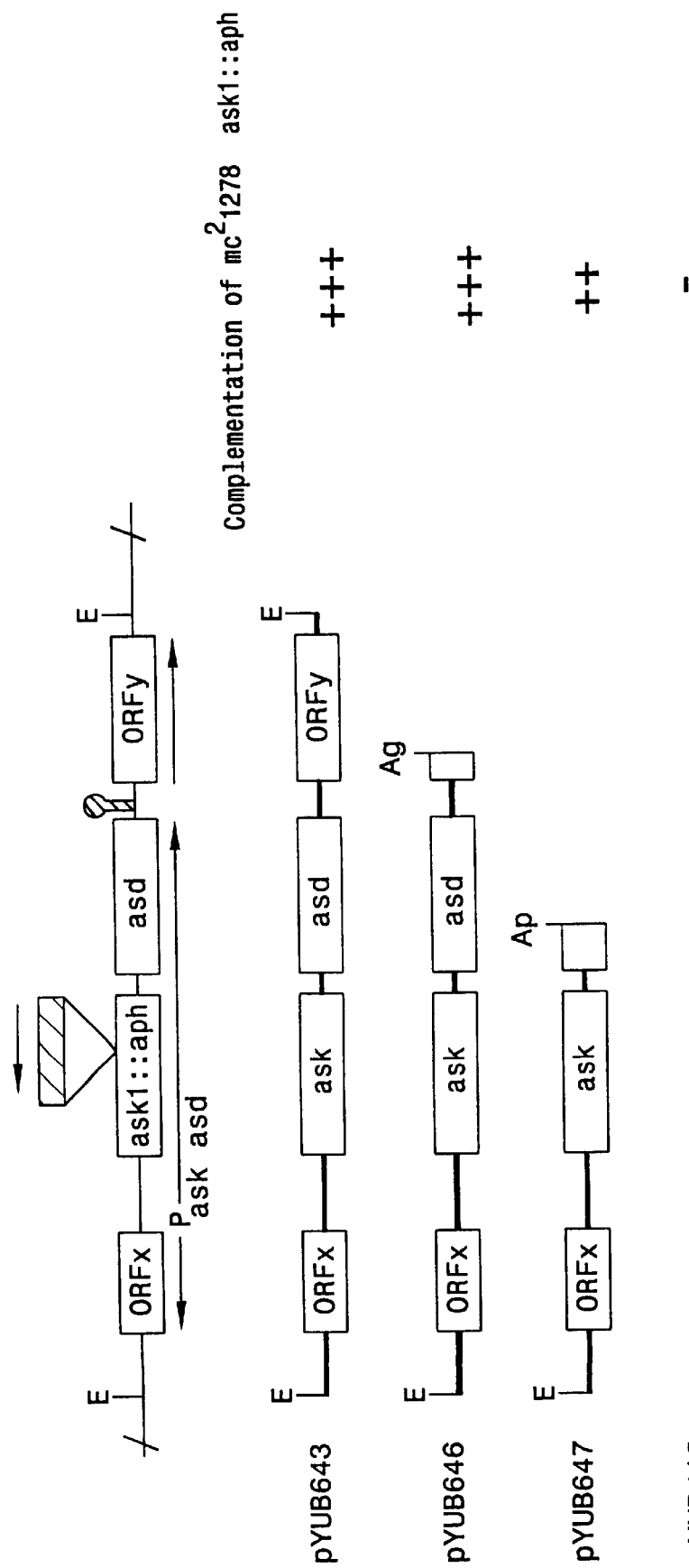

The transcriptional start site for the ask and asd genes of *M. smegmatis* has been mapped to a position 254 nucleotides upstream of the start codon of ask (18). There is a 22-bp inverted repeat downstream of asd, suggesting that the two genes constitute a operon. This operon structure is similar to that seen for the ask asd homologs of *Corynebacterium glutamicum* and *C. flavum* (Kalinowski, J., et al., *Mol. Gen. Genet.* 224:317–324 (1990), Follettie, M. T., et al., *J. Bacteriol.* 175:4096–4103 (1993)). In *M. smegmatis*, there is a divergently transcribed ORFx upstream of ask, while downstream of asd beyond the putative terminator and transcribed in the opposite direction, is ORFy (Cirillo, J. D. et al., *Molec. Microbiol.* 11:629–639 (1994)). The functions of these two open reading frames are unknown. In mc²1278, the aph insertion in ask is oriented such that the direction of transcription of aph is opposite that of the ask asd operon. As mentioned earlier, this insertion may be polar upon asd expression making the mc²1278 strain a double mutant, therefore a complementation analysis was performed upon mc²1278 to determine what effect the aph insertion had on the operon (see FIG. 5). As expected, the plasmid pYUB643 containing the full-length EcoRI fragment (ORFx ask asd ORFy), and plasmid pYUB646 (containing ORFx ask asd) complement mc²1278. Interestingly, pYUB647 which contains only ORFx and ask, could also complement the askl::aph mutation. Although growth of mc²1278 with pYUB647 on medium lacking DAP was good, it was not as robust as that seen with pYUB643 or pYUB646.

Disruption of ask in a Lysine Auxotroph of *M. smegmatis*

There is no barrier to mutation of ask or asd (or their homologs) in organisms such as *E. coli* and *Salmonella typhimurium* (Galán, et al., *Gene* 94: 29–35 (1990) and Thèze, et al., *J. Bacteriol.* 117:133–143 (1974)). Mutations within these genes results in strains auxotrophic for Met, Thr, and DAP. Mutants of *M. smegmatis* exist which are auxotrophic for Met, Thr, Ile, and Lys (McKinney, J. D., F. C. Bange, and W. R. Jacobs Jr. Unpublished (1995)), therefore DAP was focused on as the essential metabolite of this pathway. Other workers have reported an inability to obtain DAP auxotrophs of the related bacteria *Corynebacterium glutamicum* (Cremer, et al., *J. Gen. Microbiol.* 134: 3221–3229 (1988)). The explanation given for this phenomenon was that *C. glutamicum* is incapable of transporting DAP from the medium (Cremer, et al., *J. Gen. Microbiol.* 134: 3221–3229 (1988)). An absolute inability to transport DAP would not appear to be the reason for the presumed essentiality of DAP synthesis in *M. smegmatis*, as mc²155 grows well in glucose-salts minimal medium with DAP as the sole nitrogen source. Therefore, we sought another reason to explain why ask disruption and subsequent DAP auxotrophy would be lethal to *M. smegmatis*. Since meso-DAP is used for both lysine synthesis and peptidoglycan synthesis, we theorized that ask disruption is lethal to *M. smegmatis* because the extracellular meso-DAP taken up from the medium is converted to lysine, due to insufficient repression of lysA, the gene encoding DAP-decarboxylase (see FIG. 1). This hypothesis is supported by reports that expression of lysA is constitutive in the corynebacteria, close relatives of the mycobacteria (Marcel, T., et al., *Mol. Micobiol.* 4:1819–1830 (1990), Oguiza, J. A., et al., *J. Bacteriol.* 175:7356–7362 (1993)). Wild type mycobacterial cells may have a large intracellular DAP pool derived from endogenous synthesis, and the fraction converted to lysine by a low, but constitutive DAP-decarboxylase activity too small to affect peptidoglycan synthesis and cell integrity. However, a mutant with a newly disrupted ask gene, now dependent upon exogenous DAP, may not be able to transport enough DAP to achieve a intracellular DAP pool as large as that in wild type cells, thus the basal level DAP-decarboxylase activity may divert a significant fraction of the pool away from peptidoglycan synthesis leading to death of the cell.

The inventors predicted that a *M. smegmatis* Lys⁻ auxotroph unable to convert meso-DAP to lysine would accumulate a large intracellular pool of meso-DAP reserved for peptidoglycan synthesis and be permissive for ask disruption. To test this hypothesis, they compared the ability to disrupt ask in strain mc²1212 (lysA rpsL5) and strain mc²1270 (lysA⁺ rpsL5). The latter strain is an isogenic, spontaneous Lys⁺ derivative of mc²1212. Allelic exchange of ask was attempted in these strains by two methods; either by direct selection of Km$^r$ recombinants followed by identification of Km$^r$ Sm$^r$ auxotrophs, or by direct selection of Km$^r$ Sm$^r$ recombinants and screening for auxotrophy. The two strains were electroporated with pYUB609 in duplicate with one transformation mixture plated onto LB DAP Km medium, and the other plated onto LB DAP Km Sm medium. As shown in Table 2 below, both strains yielded kanamycin resistant recombinants at a similar frequency after direct selection on kanamycin medium. The number of those Km$^r$ clones that were also Sm$^r$ was higher for the Lys⁺ strain mc²1270 than for the Lys⁻ strain mc²1212. However, only the Lys⁻ strain mc²1212 yielded mutants auxotrophic for Met, Thr and DAP (Table 2). Likewise, direct selection for Km$^r$ Sm$^r$ yielded similar frequencies for recombinants from both strains, but ask disruption was only seen in the Lys⁻ strain (Table 2).

TABLE 2

Plasmid pYUB609 (ORFx askl::aph asd ORFy) chromosome recombination

| Strain | Relevant Genotype | Direct Selection for KM$^r$ | | Direct Selection for KM$^r$SM$^r$ | |
|---|---|---|---|---|---|
| | | #KM$^r$ recombinants (frequency of recombination)[a] | #KM$^r$SM$^r$ recombinants (frequency of recombination)[c] | #Km$^r$Sm$^r$ recombinants (frequency of recombination)[c] | #auxotrophs/ #KM$^r$SM$^{rd}$ |
| mc²1255 | ept-1 rspL4 | 271(4.0 × 10⁻⁴) | 2/94(0) | 13(6.5 × 10⁻⁶) | 0/13 |
| mc²1212 exp. 1 | lysA ept-4 rspL5 | 64(3.2 × 10⁻⁵) | 1/64(100) | 6(3.0 × 10⁻⁶) | 5/6 |
| exp. 2 | | 104(7.0 × 10⁻⁵) | 9/96(100) | 23(1.5 × 10⁻⁵) | 23/23 |
| mc²1270 exp. 1 | lysA⁺ ept-4 rspL5 | 616(9.0 × 10⁻⁵) | 22/150(0) | 165(2.4 × 10⁻⁵) | 0/125 |
| exp. 2 | | 500(9.3 × 10⁻⁵) | 15/150(0) | 13(1.9 × 10⁻⁵) | 0/125 |

[a,c]Each strain was electroporated in duplicate with 1 μg of pYUB609 DNA. The number of recombinant clones obtained for each type of selection is shown, along with the recombination frequencies in parentheses. These frequencies were calculated by dividing the number of clones obtained with pYUB609 by the number of Km$^r$ transformants obtained with the replicating plasmid pMV261. In these experiments, the pMV261 electroporation efficiencies ranged from 1.5 × 10⁶ to 6.8 × 10⁶ kanamycin resistant clones per 1 μg of input DNA.
[b]Number of directly-selected Km$^r$ clones that are also Sm$^r$ and the percentage of the Km$^r$Sm$^r$ clones that are auxotrophic for Met, Thr, and DAP.
[d]Number of directly-selected Km$^r$Sm$^r$ clones that are auxotrophic for Met, Thr, and DAP.

To confirm these results, a comparison was made between the ability to achieve ask disruption in isogenic Lys⁺ and Lys⁻ strains which had integrated pYUB609 (ORFx askl::aph asd ORFy) into the ask region of the chromosome. For these experiments, a Km$^r$ Sm$^s$ pYUB609 plasmid-chromosome recombinant of mc²1212 (Lys⁻) and mc²1270 (Lys⁺) from the experiment shown in Table 2 was isolated and examined. Each recombinant has pYUB609 integrated in the same fashion previously described for the ask asd chromosomal rearrangement DUP1 [(ORFx ask asd ORFy) *pYUB608*(ORFX askl::aph asd ORFy)], (see FIG. 2). The Lys⁻ strain with integrated pYUB609 is mc²1269 (lysA rpsL5 DUP1), while the Lys⁺ strain with an integrated pYUB609 is mc²1276 (lysA⁺ rpsL5 DUPl). It tested to see if the askl::aph insertion could be retained in both strains following segregation of DUP1. Duplicate cultures of strain mc²1269 (lysA rpsL5 DUP1) and strain mc²1276 (lysA⁺ rpsL5 DUPl) were grown in LBT supplemented with DAP and plated out for viable cfu/ml and colonies were tested for antibiotic resistance and auxotrophic phenotype (Table 3).

As expected, the Lys⁻ strain mc²1269 yielded Smʳ Kmʳ auxotrophic ask mutants by either direct selection for Smʳ recombinants or Smʳ Kmʳ recombinants (Table 3). The Lys⁺ strain formed Smʳ recombinants at a frequency comparable to the isogenic Lys⁻ mutant, but the frequency of Smʳ Kmʳ recombinants was slightly less. None of the Lys⁺ recombinants tested had an auxotrophic phenotype (Table 3).

To further examine the Lys⁺ phenotype as a barrier to ask disruption, we constructed a derivative of mc²1212 that is Lys⁺ due to the presence of a wild type copy of lysA. The plasmid pYUB651 was constructed from the integrating vector pYUB412 and harbors the lysA gene of *M. tuberculosis* under control of the hsp60 promoter. This plasmid was electroporated into the strain mc²1269 (lysA rpsL5 DUP1) resulting in the strain mc²1386, which is phenotypically Lys⁺. The strain mc²1269 (lysA rpsL5 DUPl) containing pYUB412 served as the Lys⁻ control strain mc²1385. The recombinants obtained from these two strains were examined after DUPl segregation in duplicate experiments done in a similar manner as previous experiments (see Table 3). We obtained Kmʳ Smʳ ask auxotrophs only from the Lys⁻ control strain mc²1385 (lysA rpsL5 DUPl attB::pYUB412). No auxotrophs were obtained from experiments using the phenotypically Lys⁺ strain mc²1386 (lysA rpsL5 DUP1 attB::pYUB651). The Smʳ Kmʳ derivatives from both strains were patched onto defined medium (Middlebrook 7H9) containing hygromycin and the appropriate supplements with or without lysine to confirm the Lys phenotype of each clone. All clones were hygromycin resistant and had maintained the Lys phenotype of their respective parental strain.

To determine if ask could be physically disrupted in the strain mc²1270, the isogenic Lys⁺ revertant of mc²1212, the products from DUP1 segregation in the strain mc²1276 (lysA⁺ rpsL5 DUP1) were analyzed, with or without an extra copy of ask asd. The experiment was essentially the same as for the mc²1255 merodiploid test. Duplicate cultures of strain mc²1387 (lysA⁺ rpsL5 DUP1 attB::pYUB412) and strain mc²1388 (lysA⁺ rpsL5 DUP1 attB::pYUB643 ask asd) were grown to late logarithmic phase in LBT DAP supplemented with Hyg, plated onto various selective media and screened for antibiotic resistance and auxotrophy. The results are shown in Table 3 below. From mc²1387 (lysA⁺ rpsL5 DUP1 attB::pYUB412) only 3% Smʳ Kmʳ clones (none of which were auxotrophs) were obtained from the directly selected Smʳ clones. None of the directly selected Smʳ Kmʳ recombinants were auxotrophic. However, from the strain mc²1388 (lysA⁺ rpsL5 DUP1 attB::pYUB643 ask asd), directly selected Smʳ recombinants yielded Smʳ Kmʳ clones at a frequency of 63%±20% (Table 3). As in the case for the wild type strain mc²1255, the Lys⁺ revertant of mc²1212 appears permissive for ask disruption only when provided with an extra copy of ask and asd.

TABLE 3

Recombination products from
DUP1 [(ORFx ask asd ORFy)* pYUB608* (ORFx ask1::aph asd ORFy)] segregation

| | | Direct Selection for Smʳ | | | Direct selection for SmʳKmʳ | |
|---|---|---|---|---|---|---|
| Strain | Relevant Genotype | Frequency of Smʳ recombinants (×10⁻³ ± SD)ᵃ | Percentage of Smʳ clones that are Kmʳ (% ± SD)ᵇ | #SmʳKmʳ/#Smʳ clones (percentage of auxotrophy)ᶜ | Frequency of SmʳKmʳ recombinants (×10⁻³ ± SD)ᵈ | #auxotrophs/# SmʳKmʳ clones e |
| mc²1266 | rspL4 DUPl attB::pYUB412 | 4.0 ± 4.5 | 3.0 ± 1.0 | 9/300 (0) | 0.12 ± 0.15 | 0/82 |
| mc²1268 | rspL4 DUPl attB::pYUB 643 (ask asd) | 1.0 ± 0.5 | 50 ± 40 | 152/300 (0) | 0.58 ± 0.38 | 0/90 |
| mc²1269 | lysA rspL5 DUPl | 6.8 ± 7.4 | 13 ± 3.0 | 20/150 (95) | 3.6 ± 2.6 | 70/75 |
| mc²1276 | lysA⁺ rpsL5 DUPl | 7.0 ± 6.9 | 0.4 ± 0.7 | 1/275 (0) | 0.34 ± 0.18 | 0/90 |
| mc²1385 | lysA rpsL5 DUPl attB::pYUB412 | 12 ± 15 | 25 ± 1.4 | 25/100 (76) | 0.10 ± 0.07 | 18/20 |
| mc²1386 | lysA rps L5 DUPl attB::pYUB 651 (lysA⁺) | 1.7 ± 1.9 | 14 ± 1.4 | 28/200 (0) | 0.04 ± 0.01 | 0/20 |
| mc²1387 | lysA⁺ rpsL5 DUPl attB::pYUB412 | 1.3 ± 0.8 | 3.0 ± 0 | 4/150 (0) | 0.07 ± 0.06 | 0/10 |

TABLE 3-continued

Recombination products from
DUP1 [(ORFx ask asd ORFy)* pYUB608* (ORFx ask1::aph asd ORFy)] segregation

| | | Direct Selection for Sm$^r$ | | | Direct selection for Sm$^r$Km$^r$ | |
|---|---|---|---|---|---|---|
| Strain | Relevant Genotype | Frequency of Sm$^r$ recombinants (×10$^{-3}$ ± SD)$^a$ | Percentage of Sm$^r$ clones that are Km$^r$ (% ± SD)$^b$ | #Sm$^r$Km$^r$/#Sm$^r$ clones (percentage of auxotrophy)$^c$ | Frequency of Sm$^r$Km$^r$ recombinants (×10$^{-3}$ ± SD)$^d$ | #auxotrophs/# Sm$^r$Km$^r$ clones e |
| mc$^2$1388 | lysA$^+$ rpsL5 DUP1 attB::pYUB 643 (ask asd) | 1.4 ± 1.6 | 63 ± 20 | 101/150 (0) | 1.9 ± 0.5 | 0/99 |

$^{a,d}$frequency of Sm$^r$ or Sm$^r$Km$^r$ recombinants was calculated by dividing the cfu/ml obtained on LB DAP Sm Km medium by the total viable cfu/ml obtained on LB DAP medium from two or three independent experiments. The averaged frequencies are reported above as n × 10$^{-3}$ ± the standard deviation.
$^b$Averaged percentage of the directly selected Sm$^r$ recombinants from multiple experiments, ± the standard deviation, that are also Km$^r$.
$^c$Number of Sm$^r$Km$^r$ recombinants obtained over the number of Sm$^r$ recombinants screened, combined from all experiments. The percentage of the Sm$^r$Km$^r$ recombinants that are auxotrophic for Met, Thr, and DAP is in parentheses.
$^e$Number of clones auxotrophic, for Met, Thr, and DAP from the directly selected Sm$^r$Km$^r$ recombinants, combined from all experiments.

"DAP-less death" of mc$^2$1278

Figure 6:
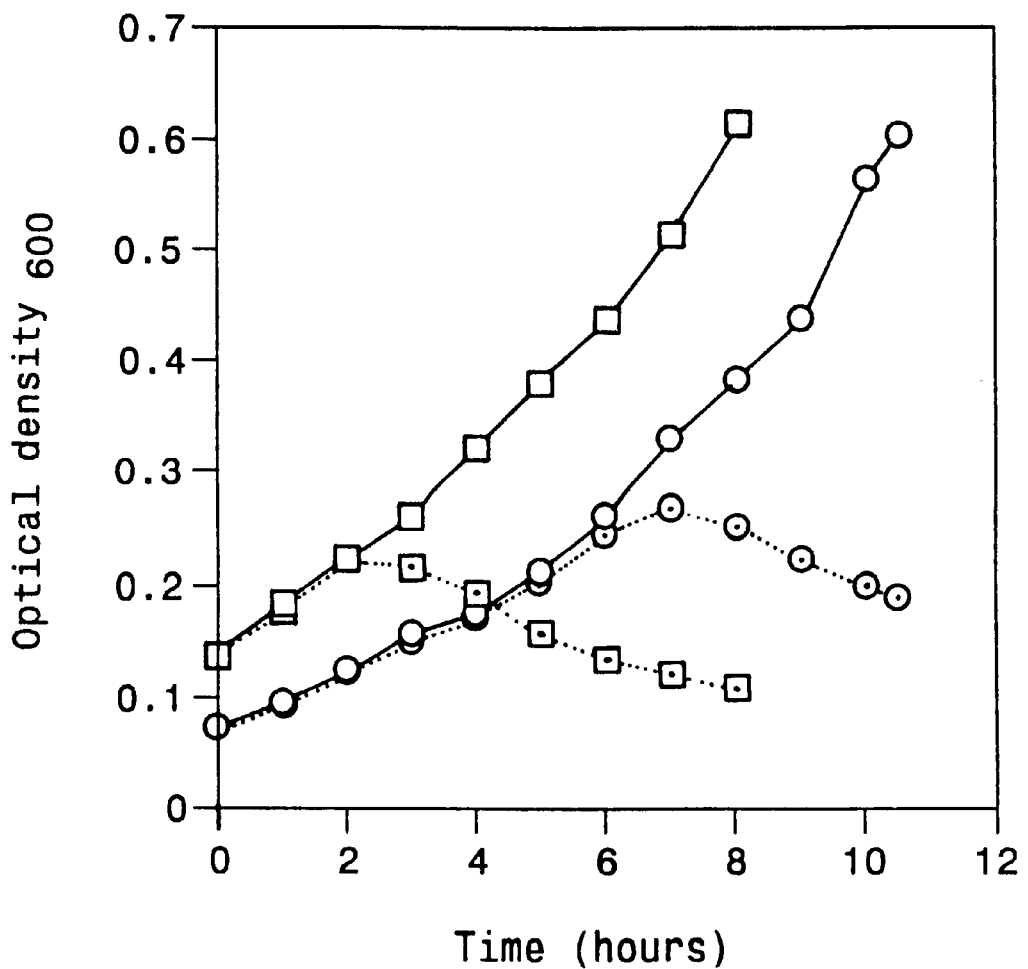
Figure 7:
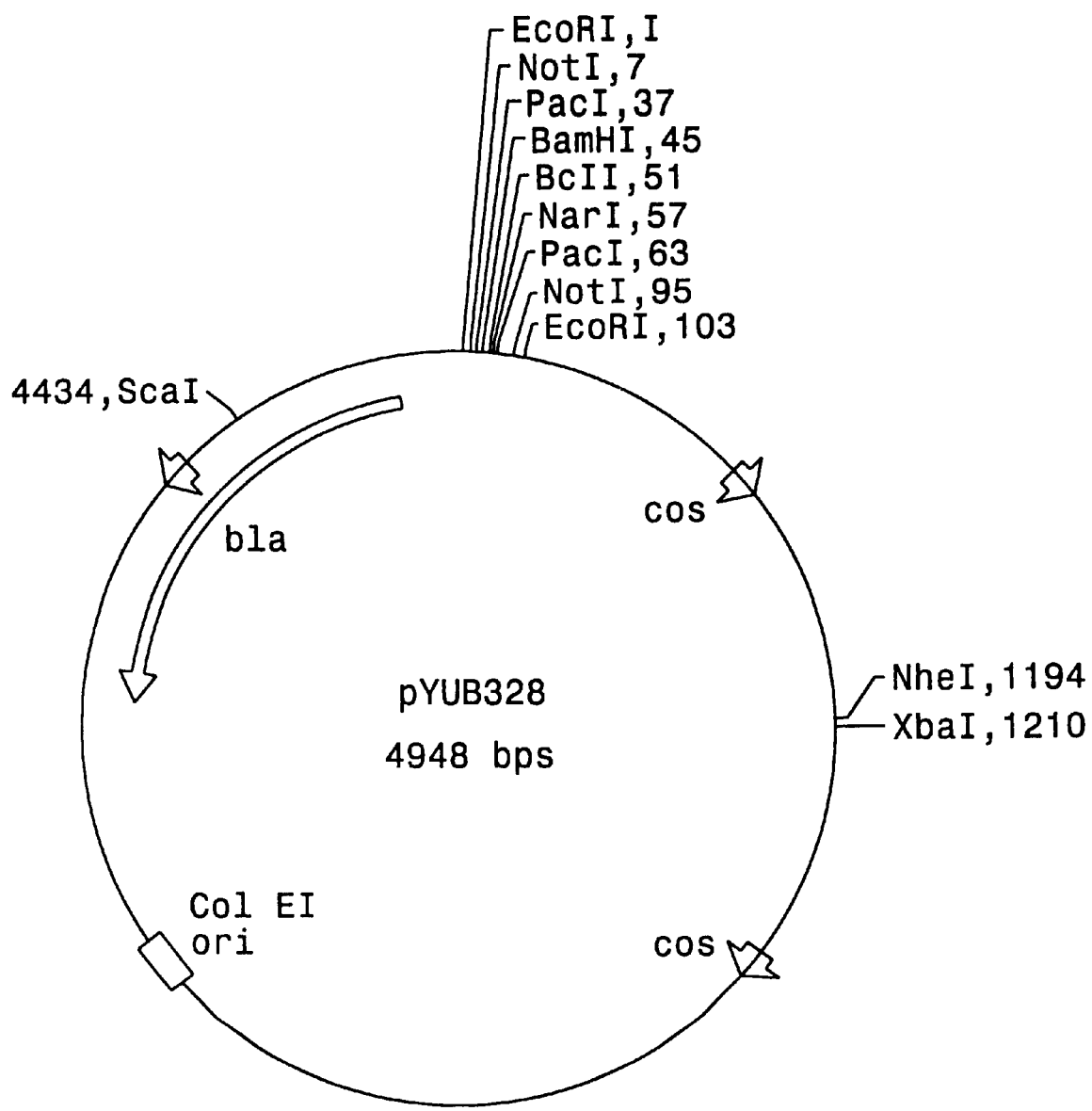

Since meso-DAP is required for lysine and peptidoglycan synthesis, it has the dual role of being important not only for protein synthesis but also maintenance of cellular integrity. DAP auxotrophs of E. coli undergo "DAP-less death" within a few generations after DAP deprivation (Rhuland, L. E., J. Bacteriol. 73:778–783 (1956), Meadow, P., et al., Biochem. J. 66:270–282 (1957)). It was tested to see if the ask mutant mc$^2$1278 would experience "DAP-less death". A mid-exponential phase culture of mc$^2$1278 was subcultured into media with or without DAP and the optical density of the cultures followed over several hours (FIG. 6). The culture containing DAP continued to grow exponentially while the culture without DAP similarly increased in density for almost 3 hours (the approximate generation time of M. smegmatis in LBT), at which time the OD$_{600}$ began to plateau then decrease rapidly. After an additional 3 hours, the OD$_{600}$ of the culture without DAP was below the initial optical density. After overnight incubation, the culture without DAP had cleared, while the culture with DAP had reached saturation. The saturated culture containing DAP was centrifuged, the cell pellet washed, resuspended and diluted into fresh LBT Km Sm medium with or without DAP and the OD$_{600}$ followed as before. These cultures did not grow exponentially until approximately 5 hours after subculture (FIG. 6). Approximately three hours into the exponential phase of growth, the density of the culture lacking DAP began to decrease with the same kinetics seen previously, while the density of the culture containing DAP increased (FIG. 6). In a fashion similar to that of E. coli, this mycobacterial DAP auxotroph lyses when deprived of DAP. The onset of this phenomenon is most rapid in exponentially growing cultures.

EXAMPLES

Example 1

Bacterial strains and culture methods

The bacterial strains used in this study are listed in Table 4. E. coli cultures were grown in LB (Luria-Bertani) broth, while M. smegmatis cultures were grown in LBT (Luria-Bertani broth containing 0.5% (w/v) Tween-80). For growth on plates, both E. coli and M. smegmatis were grown on LB agar. All cultures were incubated at 37° C. When required, the following antibiotics were used at the specified concentrations; ampicillin (50 mg/ml; E. coli), kanamycin A monosulfate (25 mg/ml; E. coli, 10 mg/ml; M. smegmatis), hygromycin B (50 mg/ml; E. coli, 150 mg/ml; M. smegmatis), streptomycin sulfate (400 mg/ml). Hygromycin B was purchased from Boehringer Mannheim (50 mg/ml in phosphate buffered saline), all other antibiotics were purchased from Sigma Chemical (St. Louis, Mo.). The preparation of kanamycin A stock solutions was based upon the activity per mg dry weight of the antibiotic, as reported by the manufacturer. Diaminopimelate (DAP), a mixture of L,L-, D,D-, and meso- isomers, (Sigma Chemical) was added to culture medium at a final concentration of 100 mg/ml from a 10 mg/ml stock solution prepared in water. For "DAP-less death" experiments, cells were grown to mid-exponential phase (OD$_{600}$~0.5) in LBT supplemented with kanamycin, streptomycin, and DAP. The culture was centrifuged and the cell pellet washed twice with LBT lacking DAP. The pellet was resuspended in a small volume of LBT and inoculated into fresh LBT Km Sm media with or without DAP. The cultures were incubated with gentle shaking (100 rpm) and the OD$_{600}$ monitored over the course of several hours.

TABLE 4

Strains used in this study

| Strain | Description |
|---|---|
| E. coli K-12 | |
| HB101 | F$^-$D(gpt-proA)62 leuB1 glnV44 ara-14 galK2 lacY1 hsdS20 rpsL20 xyl-5 mtl-1 recA13 |

TABLE 4-continued

Strains used in this study

| Strain | Description |
| --- | --- |
| M. smegmatis | |
| mc$^2$155 | ept-1 |
| mc$^2$1255 | ept-1 rpsL4 |
| P73 | lysA |
| mc$^2$1211 | lysA ept-4 |
| mc$^2$1212 | lysA ept-4 rpsL5 |
| mc$^2$1265 | ept-1 rpsL4 DUP1 [(ORFx ask asd ORFy)*pYUB608* (ORFx ask1::aph asd ORFy)] Sm$^s$Km$^r$ |
| mc$^2$1266 | ept-1 rpsL4 DUP1 [(ORFx ask asdORFy)*pYUB608* (ORFx ask1::aph asd ORFy)] attB::pYUB412 Sm$^s$Km$^r$ |
| mc$^2$1268 | ept-1 rpsL4 DUP1 [(ORFx ask asd ORFy)*pYUB608* (ORFx ask1::aph asdORFy)] attB::pYUB643 Sm$^s$Km$^r$ |
| mc$^2$1269 | lysA ept-4 rpsL5 DUP1 [(ORFxask asd ORFy)*pYUB608* (ORFx ask1::aph asd ORFy)] Sm$^s$Km$^r$ |
| mc$^2$1270 | lysA$^+$ept-4 rpsL5 |
| mc$^2$1276 | lysA$^+$ept-4 rpsL5 DUP1 [(ORFx ask asd ORFy)*pYUB608* (ORFx ask1::aph asd ORFy)] Sm$^s$Km$^r$ |
| mc$^2$1278 | lysA ept-4 rpsL5 ask1::aph |
| mc$^2$1374 | ept-1 rpsL4 DUP1 [(ORFx ask asd ORFy)*pYUB608* (ORFx ask1::aph asd ORFy)] attB::pYUB412 Km$^s$Sm$^r$ |
| mc$^2$1375 | ept-1 rpsL4 ask attB::pYUB412 Km$^s$Sm$^r$ |
| mc$^2$1376 | ept-1 rpsL4 ask1::aph attB::pYUB643 Km$^s$SM$^r$ |
| mc$^2$1377 | ept-1 rpsL4 ask attB::pYUB643 Km$^s$Sm$^r$ |

Example 2

Plasmid construction

DNA manipulations were done essentially as previously described (2). Plasmids were constructed in *E. coli* HB101 and prepared by an alkaline lysis protocol (Ish-Horowicz, D. and J. F. Burke, *Nucleic Acids Res.* 9:2989–2998 (1981)). Plasmids used for recombination experiments in *M. smegmatis* were purified using Qiagen columns as recommended by the manufacturer (Qiagen, Inc., Chatsworth, Calif.). DNA fragments used for plasmid construction were purified by agarose gel electrophoresis and recovered by absorption to glass fines (GeneClean, Bio 101, Vista, Calif.). Plasmids used in this study are listed in Table 1. The plasmid pYUB412 is an integration-proficient vector used in this work (Bardarov, S. and W. R. Jacobs Jr. 1995. Unpublished). This vector has no mycobacterial origin of replication, but instead has the mycobacteriophage L5 attachment site (attP) and the L5 integrase gene (int) (Lee, M. H., et al., *Proc. Natl. Acad. Sci.* 88:3111–3115 (1991)). In addition, pYUB412 carries the hyg gene, conferring resistance to hygromycin. This vector efficiently integrates into the phage attachment site (attB) of the *M. smegmatis* chromosome and is stable (Lee, M. H., et al., *Proc. Natl. Acad. Sci.* 88:3111–3115 (1991)).

A. Construction of the rpsL suicide vector pYUB608

The wild type rpsL gene of M. smegmatis was amplified from mc$^2$155 genomic DNA with the GeneAmp PCR kit using AmpliTaq DNA polymerase (Perkin-Elmer, Norwalk, Conn.). Oligonucleotides used as PCR primers were synthesized by the AECOM oligonucleotide synthesis facility. The oligonucleotides used for amplification of rpsL were BJ-1313 (5'-atcgttacgaggatcc-ACAAGAGAAGCAACACACAG-3') (SEQ. ID. NO.1) and BJ-1314 (5'-tcgattaggcggatcc-AGCAGGACCTTGTTCACGAG-3') (SEQ. ID. NO. 2). These primers were designed according to the previously reported DNA sequence of the rpsL gene of *M. smegmatis* (Kenney, T. J. and G. Churchward, *J. Bacteriol.* 176:6153–6156 (1994)). The capital letters designate rpsL-specific flanking DNA sequences, while the lower case letters designate the 5' extensions used to engineer unique BamHI sites (in bold) at the ends of the PCR product. BJ-1313 is specific for sequences 31-bp upstream of the start codon of rpsL, while BJ-1314 is specific for sequences 93-bp downstream of the rpsL stop codon. The two primers amplify a 528-bp fragment containing the 372-bp rpsL gene. Reaction mixtures included approximately 100 ng of template DNA, 50 pmol of each primer, and 2.0 mM MgCl$_2$. Reactions were run on a Perkin-Elmer 480 DNA thermal cycler using the following parameters: 94° C., for 5 min (1 cycle); 94° C., 1 min/55° C., 1 min/72° C., 1 min (35 cycles). The identity of the 528-bp reaction product was confirmed by restriction endonuclease mapping. The product was cloned under the control of the hsp60 promoter (via the engineered BamHI sites) in the *E. coli*-mycobacteria shuttle vector pMV261 generating pYUB600. To construct pYUB608, the rpsL gene was removed from pYUB600 with McsI and ClaI and cloned into the HincII and ClaI sites of pYUB558 (see Table 1).

B. Isolation and characterization of *M. smegmatis* rpsL mutants

The streptomycin counter selection system developed for this study required a streptomycin resistant *M. smegmatis* strain with a mutation in the rpsL gene. Since rpsL mutants of *M. smegmatis* are resistant to high levels of streptomycin (>200 mg/ml) (Kenney, T. J. and G. Churchward, *J. Bacteriol.* 176:6153–6156 (1994)), a spontaneous streptomycin resistant mutant of mc$^2$155 (mc$^2$1255) resistant to at least 500 mg/ml of streptomycin was isolated for use in these experiments. The plasmid pYUB600, bearing the wild type rpsL gene expressed from the hsp60 promoter, rendered the Sm$^r$ mutant mc$^2$1255 sensitive to streptomycin, proving that the mutation conferring streptomycin resistance in mc$^2$1255 was in the rpsL gene and that the wild type rpsL PCR product cloned in pYUB600 was functional. Subsequent experiments determined that the P$_{hps60}$rpsL construct did not confer streptomycin sensitivity upon mc$^2$1255 when present at single copy in the chromosome. This problem was overcome by cloning rpsL under the control of the major P$_{left}$ promoter taken from mycobacteriophage L5 (Nesbit, C. E., et al., *Mol. Microbiol.* 17:1045–1056 (1995)), as described above for the construction of pYUB608.

For this study the Lys$^-$ mutant strain P73 was also characterized. This strain is a nitrosoguanidine-generated mutant of *M. smegmatis* PM5. The identity of the lesion in P73 resulting in the Lys$^-$ phenotype is unknown, however we believe it to be in the lysA gene. Strain mc$^2$1211 was isolated, an efficient plasmid transformation (ept) mutant (Snapper, S. B., et al., *Mol. Microbiol.* 4:1911–1919 (1990)) of P73 and found that it could be complemented to Lys$^+$ by pYUB628, a multicopy plasmid containing the *M. tuberculosis* lysA gene driven by the hsp60 promoter. Strain mc$^2$1212, a spontaneous, high-level Sm$^r$ mutant of mc$^2$1211 was isolated and used for this work. Introduction of the wild type rpsL test plasmid pYUB600 into mc$^2$1212 rendered the strain sensitive to streptomycin, showing that the Sm$^r$ mutation of the strain was in the chromosomal rpsL gene.

C. Genetic Nomenclature

When a suicide plasmid has integrated into the chromosome via homologous recombination between the chromosome and the DNA cloned in the plasmid, a direct-order duplication of the cloned genes results with the duplicated regions joined by the vector sequences of the plasmid. To describe such strains in a clear and unambiguous fashion, specific nomenclature was used to describe chromosomal rearrangements in *Salmonella typhimurium* (Schmid, M. B. and J. R. Roth, *Genetics*. 105:517–537 (1983), Hughes, K. T. and J. R. Roth, *Genetics*. 109:263–282 (1985)). Table 1 lists the specific *E. coli* and *M. smegmatis* strains used in these studies. The designation DUP was used with a chromosome rearrangement number, followed by the genes involved in the duplication linked by the vector backbone of the suicide plasmid. For example, the integration of pYUB609 (containing the askl::aph asd region cloned in a pYUB608 vector) into the ask region of the chromosome by a single cross-over event downstream of ask is described as DUP1 [(ORFx ask asd ORFy)*pYUB608*(ORFx askl::aph asd ORFy)]. This designation clearly indicates the relative location of the mutant allele of interest and shows the type of vector used for construction of the strain.

D. Electroporation of *M. smegmatis*

Plasmid DNA was introduced into *M. smegmatis* by electroporation as previously described by Jacobs, et al, *Methods Enzymol*. 204:537–555 (1991), except that the cells were grown in LBT and chilled in ice for 5 to 15 minutes prior to washing. Freshly prepared cells were always used for recombination experiments, and LBT supplemented with DAP was added to the cells following electroporation and the mixtures incubated for four hours prior to plating.

E. Southern hybridization analysis

Genomic DNA was prepared from *M. smegmatis* strains as previously described (Jacobs Jr, W. R., et al., *Methods Enzymol*. 204:537–555 (1991)) except that glycine was added to the cultures at a final concentration of 1% (w/v) three hours prior to harvest (Balasubramanian, V., et al., *J. Bacteriol*. 178:273–279 (1996)). Southern blotting was done using the alkali denaturing procedure (Maniatis, T., et al., *Molecular cloning: a laboratory manual*. Cold Spring Harbor Laboratory, Cold Spring Harbor, N.Y. (1982)) and DNA transferred to Biotrans nylon membranes (ICN, Irvine, Calif.) by the capillary method. Hybridization and detection were done using a chemiluminescent detection system (ECL, Amersham, UK) as recommended by the manufacturer, under high stringency conditions for prehybridization and hybridization (0.1 M NaCl, 42° C.). Washes were done at 42° C. with primary wash buffer containing 6M urea and 0.1 X SSC.

---

---

What is claimed is:

1. A recombinant mycobacterium having a mutated lysA gene rendering said mycobacterium auxotrophic for lysine and at least one of a mutated aspartokinase gene or a mutated L-aspartic-β-semialdehyde dehydrogenase gene that renders said mycobacterium further auxotrophic for diaminopimelate.

2. The mycobacterium of claim 1 having a mutated aspartokinase gene that renders said mycobacterium auxotrophic for diaminopimelate.

3. The mycobacterium of claim 1 having a mutated L-aspartic-β-semialdehyde dehydrogenase gene that renders said mycobacterium auxotrophic for diaminopimelate.

4. The mycobacterium of claim 1 having both a mutated aspartokinase gene and a mutated L-aspartic-β-semialdehyde dehydrogenase gene that renders said mycobacterium auxotrophic for diaminopimelate.

5. The mycobacterium of claim 1 selected from the group consisting of *M. tuberculosis, M. paratuberculosis, M. smegmatis, M. bovis*-BCG, *M. leprae* and *M. avium.*

6. The mycobacterium of claims 1, 2, 3 or 4 wherein the gene is mutated by a method selected from the group consisting of illegitimate recombination, legitimate recombination and transposon insertion.

7. A method of producing a recombinant mycobacterium that is auxotrophic for diaminopimelate which comprises mutating the aspartokinase gene, the L-aspartic-β-semialdehyde dehydrogenase gene, or both the aspartokinase and the L-aspartic-β-semialdehyde dehydrogenase genes of a recombinant mycobacterium having a mutated lysA gene which is auxotrophic for lysine to render the mycobacterium further auxotrophic for diaminopimelate.

8. The method of claim 7 wherein the mycobacterium is selected from the group consisting of *M. tuberculosis, M. paratuberculosis, M. smegmatis, M. bovis*-BCG, *M. leprae* and *M. avium.*

9. The method of claim 7 wherein the gene is mutated by a method selected from the group consisting of illegitimate recombination, legitimate recombination and transposon insertion.

* * * * *